(12) United States Patent
Majetschak et al.

(10) Patent No.: US 7,262,162 B2
(45) Date of Patent: Aug. 28, 2007

(54) UBIQUITIN AND UBIQUITIN RELATED MOLECULES FOR TREATMENT AND PREVENTION OF HARMFUL ACTIVATION OF THE IMMUNE SYSTEM

(75) Inventors: Matthias Majetschak, Mannheim (DE); Kenneth G. Proctor, Miami, FL (US)

(73) Assignees: University of Heidelberg, Heidelberg (DE); University of Miami, Miami, FL (US)

( * ) Notice: Subject to any disclaimer, the term of this patent is extended or adjusted under 35 U.S.C. 154(b) by 402 days.

(21) Appl. No.: 10/373,196

(22) Filed: Feb. 26, 2003

(65) Prior Publication Data

US 2004/0037822 A1 Feb. 26, 2004

Related U.S. Application Data

(60) Provisional application No. 60/404,762, filed on Aug. 21, 2002.

(51) Int. Cl.
*A61K 38/00* (2006.01)
(52) U.S. Cl. .......................................... 514/2; 530/324
(58) Field of Classification Search .................... 514/2; 530/324
See application file for complete search history.

(56) References Cited

OTHER PUBLICATIONS

Ciecacute-Michalska et.al. Przeglad Lekarski, vol. 55, 5, 1998, p. 298-300.*
www.gicare.com Jackson Gastroenterology, PSC (Primary Sclerosing Cholangitis.*

Nabika et al., "Synergistic Effect Of Ubiquitin On Lipopolysaccharide-Induced TNF-Alpha Production in Murine Macrophage Cell Line RAW 264.7 Cell," Biochimica et Biophysica Acta. 1999,vol. 1450, pp. 25-34.
Asseman et al., "A Radioimmunoassay for the Quantification of Human Ubiquitin in Biological Fluids: Application to Parasitic and Allergic Diseases," Journal of Immunological Methods, 1994, vol. 173, pp. 93-101.
Majetschak et al., "Extracellular Ubiquitin Inhibits TNF-Alpha Response to Endotoxin in Peripheral Blood Mononuclear Cells and Regulates Endotoxin Hyporesponsiveness in Critical Illness," Blood, Mar. 2003, vol. 101, No. 5, pp. 1882-1890.
Majetschak et al, "Therapeutic Potential of Exogeneous Ubiquitin During Resuscitation from Severe Trauma," 2003, A.A.S.T. Webnet Domain.
Goldstein, Gideon et al., "Isolation of a Polypeptide . . . ", Proc. Natl. Acad. Sci. USA, vol. 72 No. 1, pp. 11-15, Jan. 1975.
Szewczuk, Zbigniew et al., "Immunosuppressory Activity . . . ", Biopolymers vol. 74, 352-362 (2004).
Earle, Steven et al., "Ubiquitin reduces fluid shifts . . . ", Surgery, 2005, vol. 138:431-438.
Ciećko-Michalska, Irena et al., "Primary sclerosing cholangitis . . . ", Med Sci Monit, 1997: 3(2): 238-241.
Zdzislaw, Zak et al., "Immunochemical and physicochemical prosperties . . . Part 1", Dept of Animal Biochemistry, Institute of Molecular Biology, Materia Medica Poland, Fasc. 2 (39).
Zdzislaw, Zak et al., "Immunochemical and physicochemical properties . . . Part 2", Dept of Animal Biochemistry, Institute of Molecular Biology, Materia Medica Poland, Fasc. 2 (39).
Manuscript: Majetschak, Matthias, "Brief Report: Prolongation of skin graft survival by exogenous ubiquitin", pp. 1-16 with attached Figure.

* cited by examiner

*Primary Examiner*—Cecilia J. Tsang
*Assistant Examiner*—Maury Audet
(74) *Attorney, Agent, or Firm*—Ann S. Hobbs; Venable LLP

(57) ABSTRACT

Compositions and methods for suppressing the immune system of a mammal using ubiquitin and derivatives and analogs thereof.

20 Claims, 9 Drawing Sheets

UBIQUITIN AND UBIQUITIN RELATED MOLECULES FOR TREATMENT AND PREVENTION OF HARMFUL ACTIVATION OF THE IMMUNE SYSTEM

This application claims priority to U.S. provisional application No. 60/404,762, filed Aug. 21, 2002, which is hereby incorporated by reference.

The work leading to the invention described and claimed herein was carried out using funds from Grant no. ONR-N-000-14210338 from the Office of Naval Research and MA 2474/1-1 from the Deutsche Forschungsgemeinschaft (DFG). The U.S. government and DFG have certain rights in the invention.

BACKGROUND OF THE INVENTION

1. Field of the Invention

The invention relates to compositions and methods for suppressing the immune system of a mammal using ubiquitin and derivatives and analogs thereof.

2. Background Information

Ubiquitin, a small (8.6 kDa), heat stable and highly conserved 76 amino acid protein in all eukaryotic cells was originally identified as an immunopoetic polypeptide from thymocytes [1,2]. Further research has suggested that ubiquitin plays a key role in essential intracellular functions such as cell differentiation, cell cycle control, heat shock response, and regulation of immune responses [3–5]. Traditionally, the most important function of ubiquitin was considered to be regulation of protein turnover by the ubiquitin-proteasome-pathway [3–6]. There is no known physiologic function for extracellular ubiquitin, even though it is normally present in the extracellular space. Significantly increased ubiquitin levels above normal have been described in serum or plasma during parasitic infections [7], in alcoholic liver cirrhosis [8], type 2 diabetes [9], hairy cell leukemia [10], and in patients with renal failure and hemodialysis treatment [11,12]. In various in vitro conditions, extracellular ubiquitin can alter lymphocyte differentiation, inhibit IgG production in splenocyte cultures, and regulate growth and amyloid formation in hematopoietic cells [1,10,13,14,16]. In a murine macrophage cell line (RAW 264.7), ubiquitin potentiates endotoxin (LPS) induced TNF production [15]. Otherwise, the function of extracellular ubiquitin is unknown.

The present application discloses a new biological function of extracellular ubiquitin and demonstrates that 1) exogenous ubiquitin acts as a cytokine-like protein with anti-inflammatory properties and 2) administration of exogenous ubiquitin prevents sequelae of a harmful activation of the immune system in vivo.

SUMMARY OF THE INVENTION

The present invention provides compositions and methods for using ubiquitin and derivatives and analogs thereof to suppress the immune system of a mammal. The inventors have found that systemic administration of commercially available ubiquitin, a heat stable and highly conserved 76 amino acid protein (8.6 kDa), prevents the sequelae of a harmful activation of the immune system of a mammal. Because ubiquitin can be covalently linked to either ubiquitin itself or other proteins and its structure is highly conserved, a similar action is expected for other ubiquitin-related and ubiquitin-derived molecules. Ubiquitin-related molecules include, for example: UBLs; ubiquitin-like proteins (e.g. SUMO1, NEDD8, Rad23, Elongin B, Parkin); proteins with homology to ubiquitin in amino acid composition or structure; proteins containing ubiquitin-like domains (such as UBD domains (also called UbL or UBQ), defined by a stretch of 45–80 residues with significant sequence homology to ubiquitin, or UBX domains, which reveal a close structural relationship to ubiquitin). Ubiquitin-derived molecules include, for example: ubiquitin-protein conjugates, di- to multiple-ubiquitin chains, chemically modified ubiquitins, such as methylated ubiquitin, ubiquitin aldehyde, ubiquitin K48R or ubiquitin$^{+1}$.

The methods and compositions of the invention are useful, inter alia, for the treatment and prevention of sepsis and multiple organ failure, fluid extravasation/capillary leakage (edema formation) in burn patients, reducing the fluid requirement in trauma, shock and burn patients and organ rejection in organ transplantation patients; treatment of cancer; treatment of viral and autoimmune diseases; treatment of inflammatory bowel diseases (Morbus Crohn, Colitis ulcerosa); treatment of polyarthritis; and treatment and prevention of adverse effects of chemotherapeutics.

In one embodiment, it is an object of the invention to provide a method of inducing immunosuppression in a mammal comprising administering to the mammal an effective amount of ubiquitin, or a fragment, analog or derivative thereof.

As used herein, the term "fragment" is intended to mean a contiguous segment of at least 5, preferably at least 10, more preferably at least 15, and most preferably at least 20 amino acid residues of ubiquitin.

As used herein, the term "analog" is intended to mean proteins with homology to ubiquitin in amino acid sequence or three dimensional structure (UbLs; ubiquitin-like domains).

As used herein, the term "derivative" is intended to mean a natural or synthetic modification of ubiquitin, for example, a ubiquitin-protein conjugate, di- to multiple-ubiquitin chains, chemically modified ubiquitins, such as methylated ubiquitin, ubiquitin aldehyde, ubiquitin K48R or ubiquitin$^{+1}$.

Effective amounts of ubiquitin and related compounds (i.e. analogs and derivatives) are amounts that are sufficient to bring about an efficacious clinical effect, and can be determined by those of skill in the art by routine experimentation. In general, an effective dosage of ubiquitin for the purposes of this invention is expected to be about 0.01 to 10 mg/kg body weight, preferably 0.05 to 5 mg/kg body weight, more preferably 0.1 to 5 mg/kg body weight and most preferably 0.1 to 1 mg/kg body weight. Analogs and derivatives should have similar ranges of efficacy based on their relative molecular weights.

Ubiquitin can be administered by any means known to be suitable to those of skill in the art, including oral, intraperitoneal, intranasal, intravenous, subcutaneous, intradermal, and intramuscular administration, with the preferred route being intravenous.

Ubiquitin and its fragments, derivatives and analogs, may be administered alone, or in a pharmaceutical composition including carriers and excipients. Suitable carriers and excipients are known in the art and are described in generally known publications, for example Remington's Pharmaceutical Sciences, 18th ed., Mack Publishing Co., Easton, Pa. (1990). Accordingly, also included in the invention is a class of pharmaceutical compositions comprising ubiquitin, or a fragment, analog or derivative thereof. Such compositions are useful for treatment of conditions as described herein and other conditions wherein immunosuppression is desirable.

It is well known that activation of the immune system plays a role in many pathological conditions. Examples of such conditions include autoimmune diseases, allograft reaction resulting in graft vs. host or host vs. graft disease, and sequellae of tissue damage, severe infections and sepsis including endotoxic shock, and pancreatitis.

Thus, the present invention provides a method of treating a subject suffering from an autoimmune disease, comprising administering an effective amount of ubiquitin, or a fragment, analog, or derivative thereof, to prevent, alleviate or suppress the symptoms of an autoimmune disease. Such autoimmune diseases may be organ-specific or non-organ-specific. Examples of such autoimmune diseases include multiple sclerosis, rheumatoid arthritis, Crohn's disease, colitis ulcerosa and aplastic anemia systemic lupus erythematosus (SLE or lupus), dermatomyositis, pernicious anemia, Addison's disease, ankylosing spondylitis, antiphospholipid syndrome, Churg-Strauss Syndrome, discoid lupus, fibromyalgia, Grave's Disease, juvenile arthritis, myasthenia gravis, psoriasis, Raynaud's phenomenon, Reiter's Syndrome, rheumatic fever, sarcoidosis, scleroderma, Sjögren's Syndrome, stiff-man syndrome, Takayasu arteritis, temporal arteritis/giant cell arteritis, uveitis, vasculitis, vitiligo, and Wegener's granulomatosis.

In a further embodiment, the invention provides a method of inhibiting the effects of allograft reaction in human subjects. In particular, ubiquitin and related compounds can be used according to the invention to modulate immune responses to allografts where untreated rejection would otherwise lead to graft loss. Thus, the invention provides a method of preventing organ graft rejection in a subject in whom an organ has been transplanted, for example a kidney, pancreas, liver, lung, heart or bone marrow. The invention also provides a method of preventing or treating graft vs. host disease.

In yet a further embodiment, the invention provides a method of treating and preventing diseases, sequelae or pathological conditions mediated by an activation of the immune system in a mammal comprising administering to said mammal an effective amount of ubiquitin, or a fragment, analog or derivative thereof. Such diseases, sequelae and pathological conditions include, inter alia, capillary leakage, pulmonary failure, sepsis, endotoxic shock, sequelae of tissue damage. Such conditions particularly include the sequelae of major tissue damage.

These and other aspects and embodiments of the invention can be understood more fully with the aid of the detailed description and examples set forth below.

BRIEF DESCRIPTION OF THE DRAWINGS

FIG. 1A shows dose-dependent inhibition of TNFα secretion of human whole blood by exogenous ubiquitin. Whole blood cultures (in duplicates) from healthy donors (n=13–18) were incubated for 4 h with 0–1 µg/mL exogenous ubiquitin in the presence of 100 ng/mL LPS. Data represent mean±SEM. *: P<0.05 vs. cultures without ubiquitin.

FIG. 1B shows dose-dependent inhibition of TNFα secretion of human PBMNCs by exogenous ubiquitin. PBMNC cultures (in duplicate) from healthy donors (n=10–15) were incubated for 4 h with 0–1 µg/mL exogenous ubiquitin in the presence of 100 ng/mL LPS. Data represent mean±SEM. *: P<0.05 vs. cultures without ubiquitin.

FIG. 1C shows kinetics of the LPS stimulated TNFα secretion of human whole blood in the presence of 0 (□), 500 ng/mL (■) and 1000 ng/mL (●) exogenous ubiquitin. Cultures (in duplicate) were incubated for 2 h, 4 h, 8 h and 16 h.

FIG. 1D shows kinetics of the LPS stimulated TNFα secretion of $10^5$ human PBMNC in the presence of 0 (□), 500 ng/mL (■) and 1000 ng/mL (●) exogenous ubiquitin. Cultures (in duplicate) were incubated for 2 h, 4 h, 8 h and 16 h.

FIG. 1E shows TNFα mRNA levels in human PBMNCs stimulated with 100 ng/mL LPS in the presence of 0, 500 and 1000 ng/mL ubiquitin for 2 h. *: P<0.05 vs. stimulation without ubiquitin.

FIG. 1F shows dose dependent inhibition of TNFα secretion of porcine (■) and murine (■) whole blood by exogenous ubiquitin. Whole blood cultures (in duplicates) (n=3) were incubated for 4 h with 0–1 µg/mL exogenous ubiquitin in the presence of 100 ng/mL (porcine) and 1 µg/mL (murine) LPS. Data represent mean±SEM. *: P<0.05 vs. cultures without ubiquitin.

FIG. 2A shows Ubiquitin serum and urine concentrations in healthy volunteers and critically ill patients. The boxes extend from the $25^{th}$ to $75^{th}$ percentile, the horizontal line shows the median. Whiskers show the range of data. Data are measurements of ubiquitin concentrations in serum samples from 35 healthy uninjured donors, 23 severely injured blunt trauma patients on the day of admission and 24 sepsis patients. Ubiquitin urine concentrations were determined in specimen from 19 sepsis patients and 10 healthy individuals. *: P<0.05 vs. concentrations in healthy volunteers' specimen.

FIG. 2B demonstrates detection of free ubiquitin in serum specimen by immunoblotting. Serum proteins were separated by SDS-PAGE, transferred to PVDF membranes and probed for ubiquitin with anti-ubiquitin AS (1:200). Lane 1: Healthy donors' serum (15 µg), lane 2–5: Patients' serum (lane 2: 10 µg, lane 3: 15 µg, lane 4: 20 µg, lane 5: 25 µg), lane 6: Ubiquitin (10 ng). Ub: Ubiquitin.

FIG. 2C shows detection of free ubiquitin in urine (10 µL) by immunoblotting. Lane 1: Ubiquitin (5 ng), lane 2: healthy donors' specimen, lane 3 and 4: Patients' specimen. Ub: Ubiquitin.

FIG. 3A shows ubiquitin serum concentrations in volunteers (n=12) and trauma patients (n=10) during 14-days after trauma. Date represent mean±SEM.

FIG. 3B shows LPS induced whole blood TNFα secretion in the same volunteers and trauma patients as FIG. 3A. Whole blood cultures were incubated for 4 h in the presence of 100 ng/mL LPS. Data represent mean±SEM.

AS: Anti-ubiquitin AS diluted $1:10^3$, $1:10^2$ and 1:10 in the cell cultures. Ub P4D1 and Ub N-19: Diluted $1:10^3$ in the cell cultures.

Figure 4:
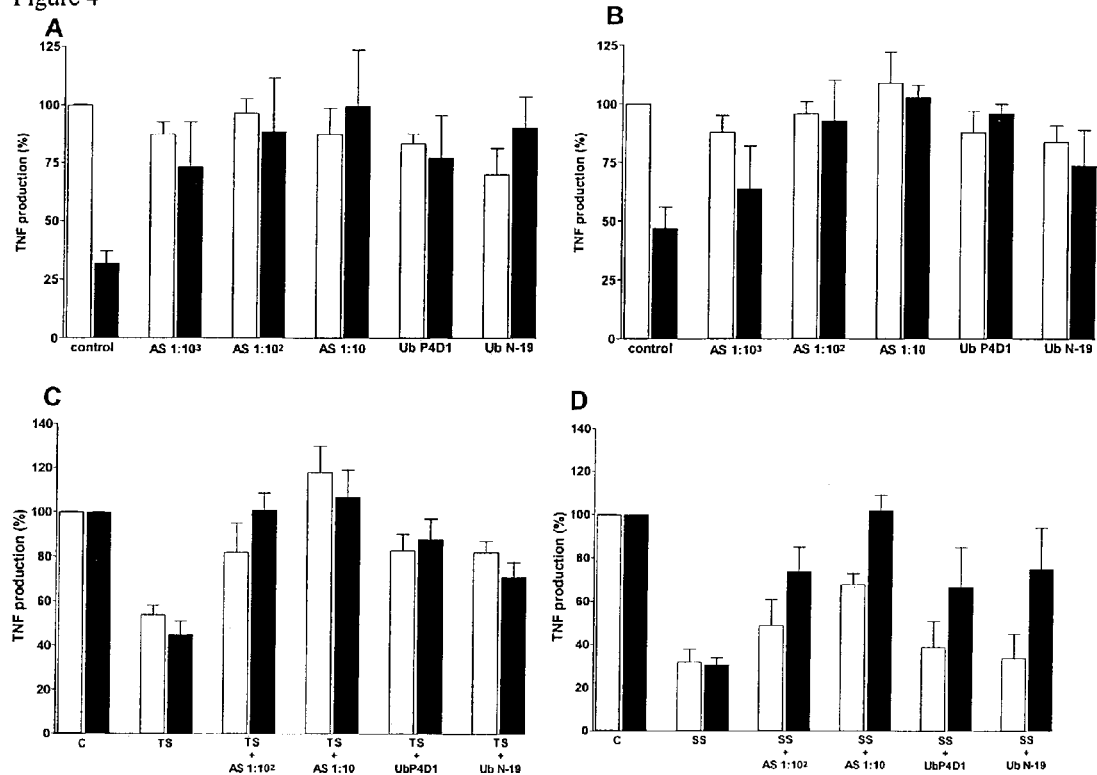
FIGS. 4A–B show that anti-ubiquitin Ab neutralize the inhibitory activity of ubiquitin on LPS induced whole blood (4A) and PBMNC (4B) TNFα production. TNF production (%): % of the TNFα secretion in cultures without exogenous ubiquitin and without antibodies. Data represent mean±SEM from 3 different whole blood and PBMNC cultures obtained from healthy volunteers. Cultures without (□) or with 500 ng/mL exogenous ubiquitin (■) in the presence of LPS (100 ng/mL for 4 h). Control: Cultures without addition of Ab.

FIGS. 4C–D show the effect of anti-ubiquitin Ab on the inhibitory activity of trauma (4C) and sepsis (4D) patients' serum on LPS induced TNFα production of whole blood and PBMNCs. Whole blood (□) and PBMNCs (■) were cultured with 100 ng/mL LPS for 4 h. TNF production (%): % of the TNFα secretion in cultures containing additional healthy volunteers' serum (30% (v/v) in the cell culture mixture) without antibodies. Data represent mean±SEM from 4 different cultures obtained from healthy volunteers. C: control, healthy volunteers' serum. TS: Trauma patients' serum (n=4, 30% (v/v) in the cell culture mixture). SS: Sepsis patients' serum (n=4, AS: 30% (v/v) in the cell culture mixture). Anti-ubiquitin AS diluted $1:10^2$ and 1:10 in the cell cultures. Ub P4D1 and Ub N-19: Diluted $1:10^3$ in the cell cultures.

Figure 5:
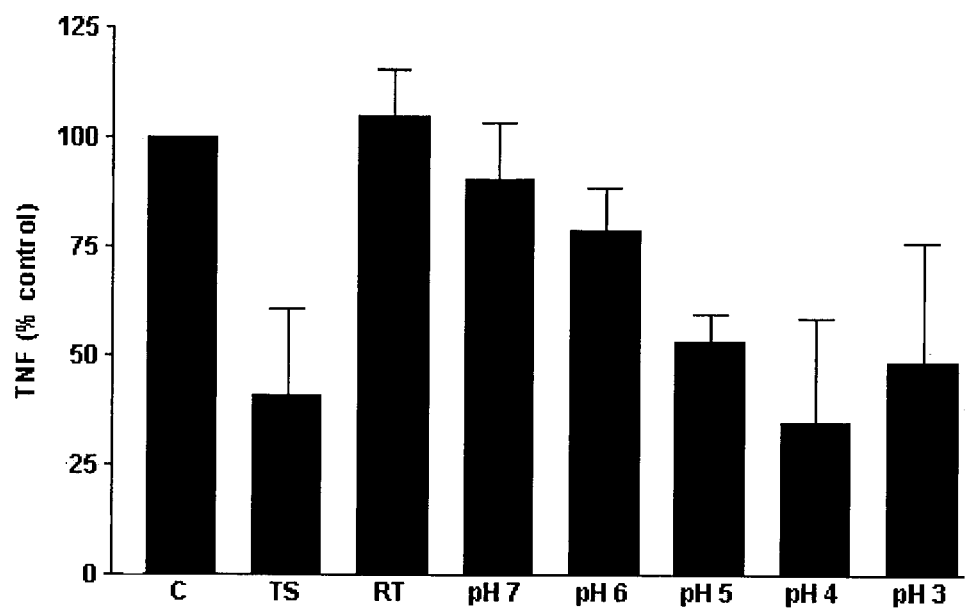
Figure 5:
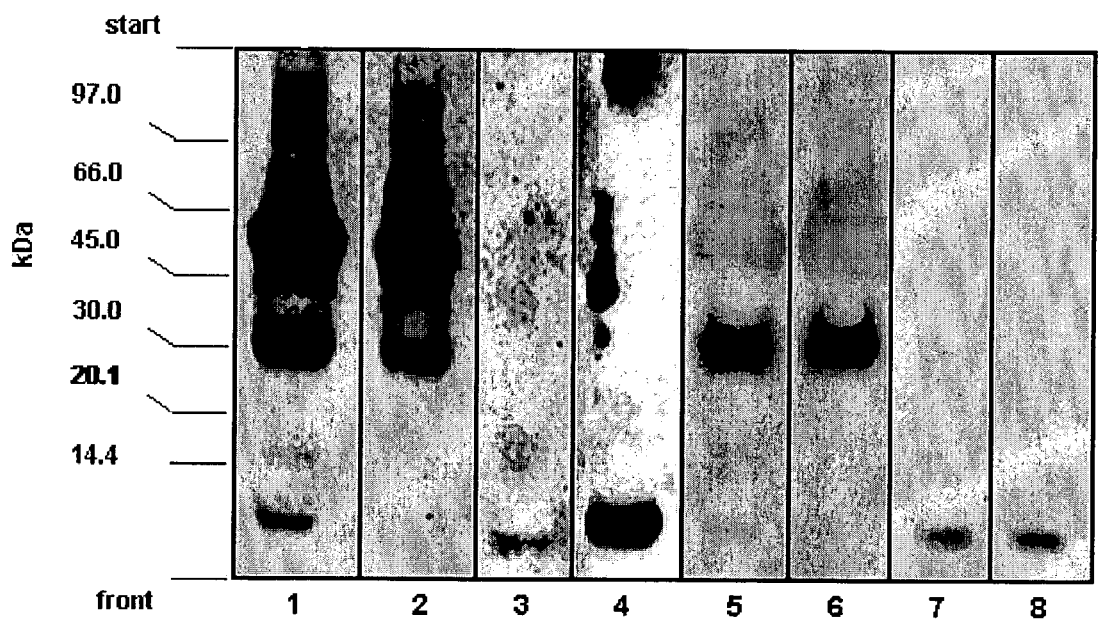

FIG. 5A shows TNF levels when serum from trauma patients and controls was applied to an anti-ubiquitin antibody column and the adsorped protein was eluted by acidification. Run-through and elutions were collected and tested for inhibitory activity of LPS induced TNFα production in healthy donors' whole blood. Whole blood cultures were incubated with the fractions (50% (v/v) in the cell culture mixtures) obtained by affinity chromatography in the presence of LPS for 4 h in a constant volume of 200 µL. Data (% control) are mean±SD of the TNFα secretion in the cell culture supernatants from two experiments (in duplicates). C: control, cell culture in the presence of 25% additional volunteers' serum in a constant volume of 200 µL. TS: Cell culture in the presence of 25% trauma patients' serum in a constant volume of 200 µL. RT: Cell cultures containing the run-through fraction. pH 7–3: Cell cultures containing the eluted fractions.

FIG. 5B shows immunoblot analysis of the fractions obtained by anti-ubiquitin affinity chromatography. Fractions were separated by SDS-PAGE, transferred to PVDF membranes and probed for ubiquitin with anti-ubiquitin AS (1:200; lanes 1–4) and monoclonal UbP4D1 (1:500; lanes 5–8). Lane 1: Patient serum, 10 µg. Lane 2: Run-through, 20 µg. Lane 3: pH 3/4 eluate, 20 µL. Lane 4: Ubiquitin, 10 ng. Lane 5: Patient serum, 50 µg. Lane 6: Run-through, 50 µg. Lane 7: pH 3/4 eluate, 200 µL of pH 3/4 eluate 10-fold concentrated by boiling. Lane 8: Ubiquitin 80 ng.

FIGS. 6A–B show the effect of anti-ubiquitin antibodies on LPS induced TNFα secretion of multiply injured (6A) and sepsis (6B) patients' blood. Whole blood was incubated with LPS (100 ng/mL) for 4 h. AS: Anti-ubiquitin AS diluted $1:10^2$ and 1:10 in the cell cultures. Ub P4D1 and Ub N-19: Diluted $1:10^3$ in the cell cultures. Volunteers: Whole blood cultures from healthy donors. TNF production (%): % of the TNFα secretion in trauma (6A) and sepsis (6B) patients' whole blood incubated without antibodies. Values are mean±SEM from 5 healthy donors', 5 trauma and 5 sepsis patients.

FIG. 6C shows the effect of anti-ubiquitin AS (1:10) on LPS induced TNFα secretion of uninjured donors', trauma and sepsis patients' blood. Individual values from FIGS. 6A and 6B are plotted.

Figure 7:
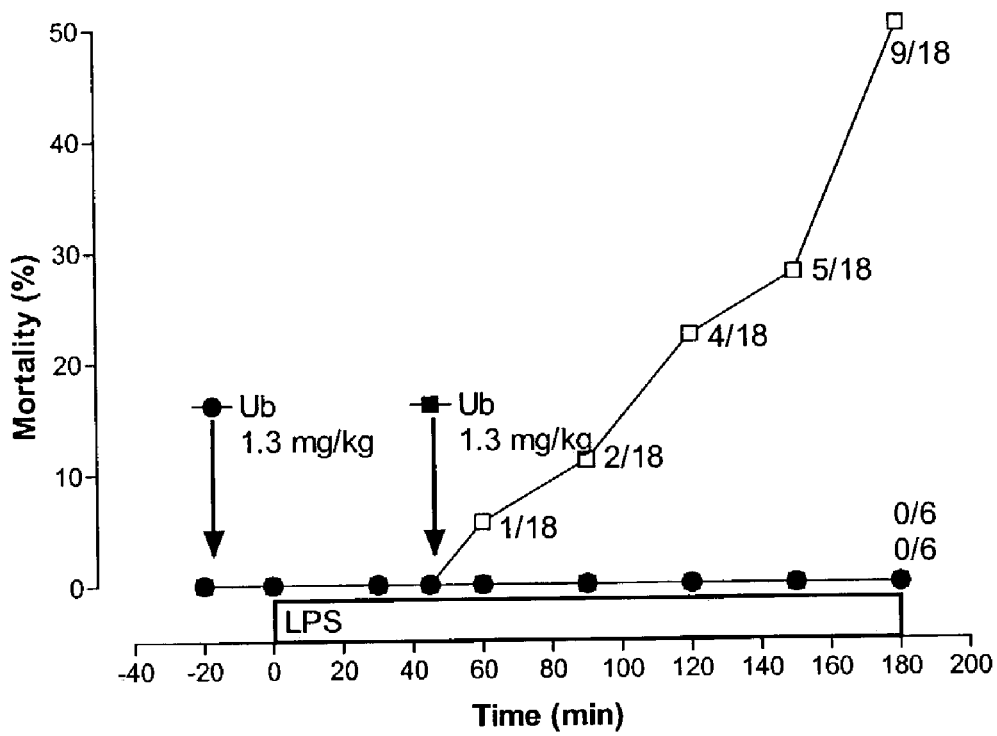

FIG. 7 shows percent mortality over time in animals receiving either 1.3 mg Ub/kg body weight (n=6) at t=0 min (●), 1.3 mg Ub/kg body weight (n=6) at t=45 min (■) or placebo (BSA; 0.13 mg/kg body weight (□; n=9–18). At time point t=0 min, 0.5 µg endotoxin/kg body weight was infused for 3 hr.

Figure 8:
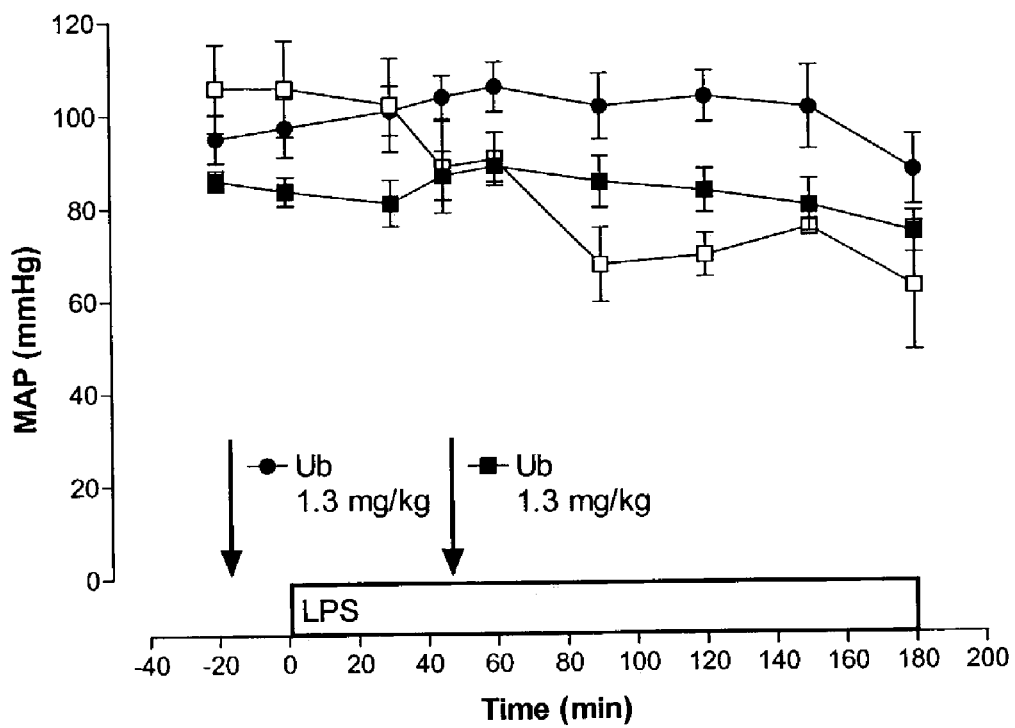

FIG. 8 shows the timecourse of MAP in animals that received either 1.3 mg Ub/kg body weight (n=6) at t=0 min (●), 1.3 mg Ub/kg body weight (n=6) at t=45 min (■) or placebo (BSA; 0.13 mg/kg body weight (□; n=9–18). At time point t=0 min, 0.5 µg endotoxin/kg body weight was infused for 3 hr.

Figure 9:
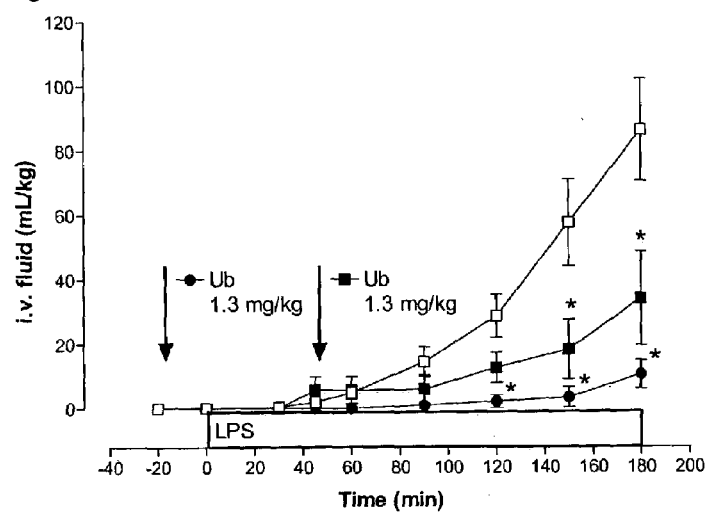

FIG. 9 shows I.V. fluid (cumulative volume/kg body weight) necessary to maintain MAP at greater than 70 mmHg after administration of either 1.3 mg Ub/kg body weight (n=6) at t=0 min (●), 1.3 mg Ub/kg body weight (n=6) at t=45 min (■) or placebo (BSA; 0.13 mg/kg body weight (□; n=9–18). At time point t=0 min, 0.5 µg endotoxin/kg body weight was infused for 3 hr. *: p<0.05 vs. BSA (ANOVA).

Figure 10:
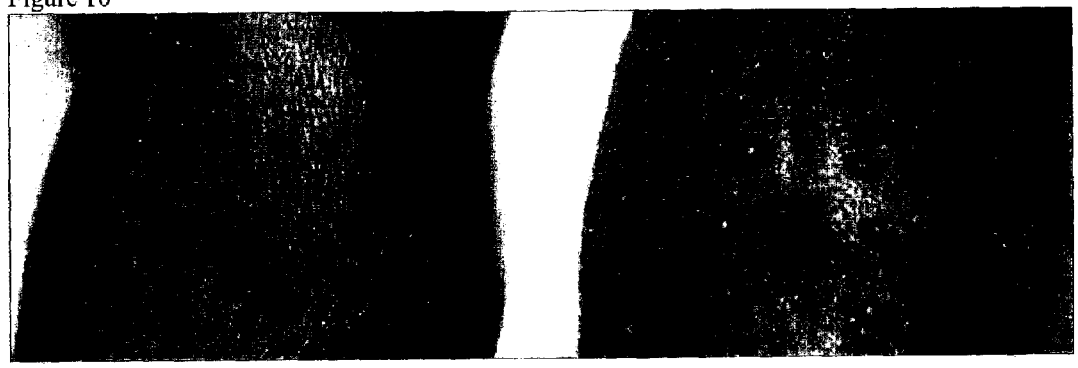

FIG. 10 shows typical clinical appearance at the end of the observation period (180 min) following i.v. endotoxin infusion. Left: animal of the ubiquitin pre-treatment group (no or slight erythema, no edema). Right: animal of the control group (massive erythema and bright edema).

Figure 11A:
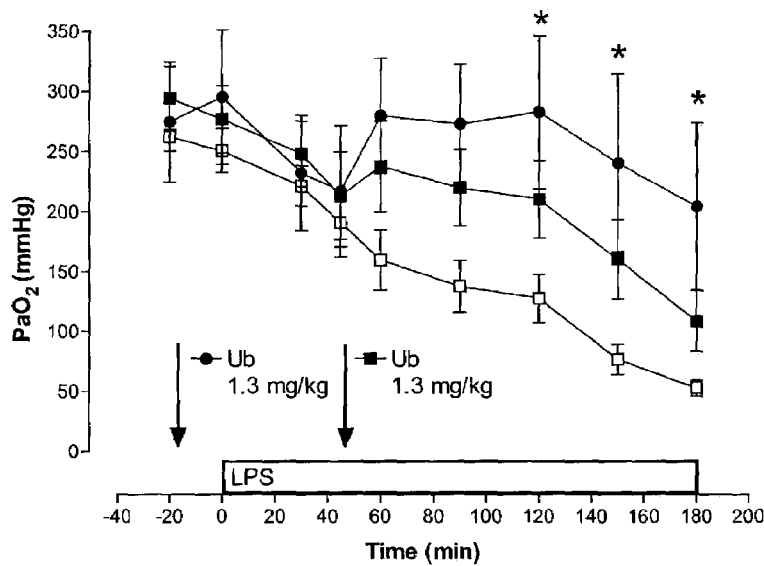

FIG. 11A shows $PaO_2$ following i.v. endotoxin infusion with either 1.3 mg Ub/kg body weight (n=6) at t=0 min (●), 1.3 mg Ub/kg body weight (n=6) at t=45 min (■) or placebo (BSA; 0.13 mg/kg body weight (□; n=9–18). At time point t=0 min, 0.5 µg endotoxin/kg body weight was infused for 3 hr. *: p<0.05 vs. BSA (ANOVA).

Figure 11B:
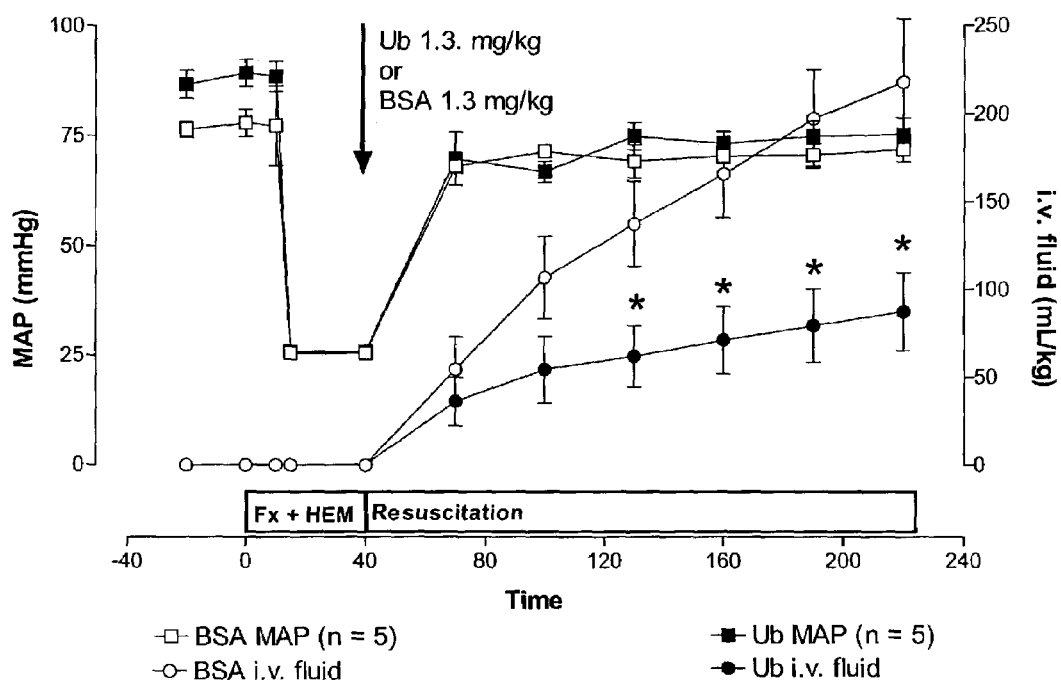

FIG. 11B shows MAP after bilateral femur fracture and a 30 min shock period. Animals received either 1.3 mg Ub/kg body weight (n=5) or placebo (BSA; 0.13 mg/kg body weight; n=5) followed by resuscitation with Lactated Ringer's to a MAP of ≧70 mmHg. I.v. fluid: cumulative volume/kg body weight. *: p<0.05 vs. BSA (ANOVA).[00045]

Figure 12:
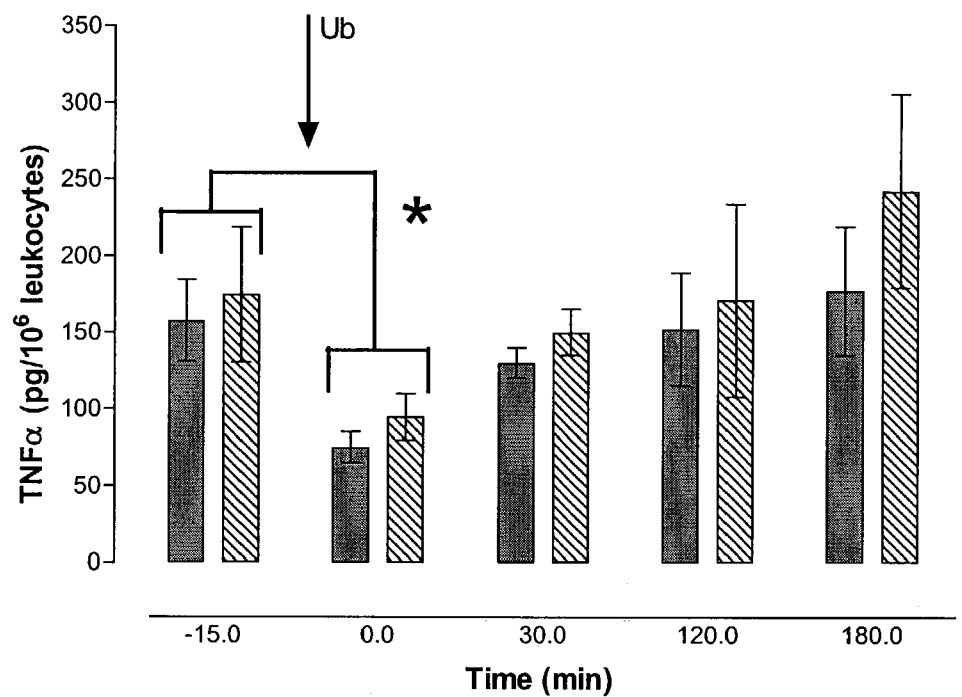

FIG. 12 shows endotoxin evoked TNFα production of blood after infusion of 1.3 mg/kg ubiquitin. Whole blood was drawn and stimulated with 100 ng/mL (grey bars) and 1000 ng/mL (striped bars) endotoxin for 18 hrs. After baseline data were collected (t=−15 min) ubiquitin was infused. Data (mean±SEM; n=4) are expressed as pg TNFα/ $10^6$ leukocytes. *: p<0.05 vs. TNFα production at t=−20 min.

Figure 13:
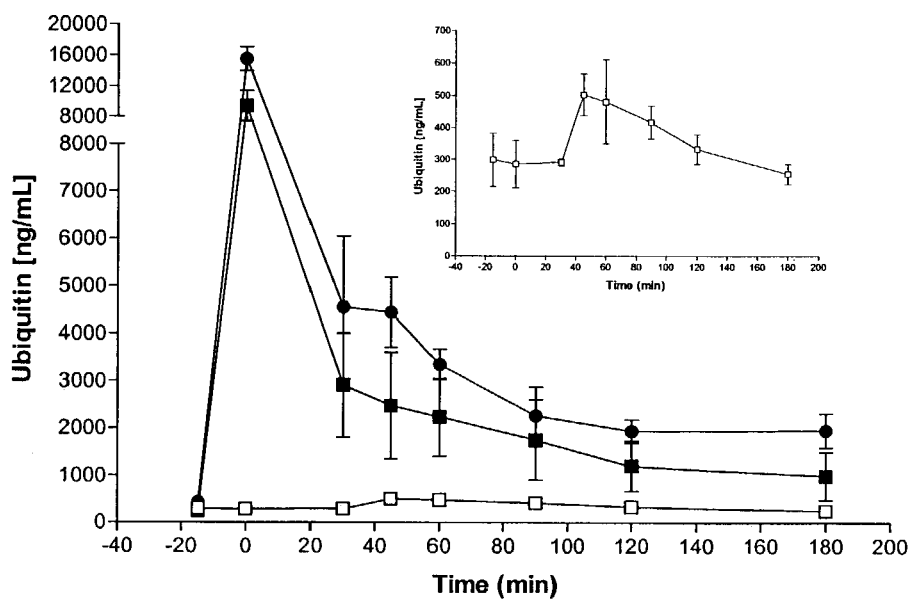

FIG. 13 shows ubiquitin serum levels following i.v. bolus injection of ubiquitin. Control group (●: 1.3 mg Ub/kg body weight at t=−15 min, no endotoxin infusion; n=3); ubiquitin pre-treatment group (■: 1.3 mg Ub/kg body weight at t=−15 min, 0.5 µg/kg body weight endotoxin for 3 hr at t=0 min; n=3); placebo group (□: 1.3 mg BSA/kg body weight at t=−15 min, 0.5 µg/kg body weight endotoxin for 3 hr at t=0 min; n=3). Insert: Ubiquitin serum levels in the placebo group (□: 1.3 mg BSA/kg body weight at t=−15 min, 0.5 µg/kg body weight endotoxin for 3 hr at t=0 min; n=3).

DETAILED DESCRIPTION OF THE INVENTION

The invention is supported by the following in vitro and in vivo findings:

I. Exogenously administered ubiquitin reduces TNFα production of endotoxin stimulated isolated peripheral blood mononuclear cells and of endotoxin stimulated whole blood.

II. Critically ill patient blood contains 5–7 fold increased levels of ubiquitin when compared with healthy individuals.

III. Neutralization of ubiquitin or depletion of endogenous ubiquitin in trauma and sepsis patient blood restores reduced TNFα producing capacity.

IV. Systemic administration of ubiquitin prevents death after an otherwise lethal endotoxic challenge.

V. Systemic administration of ubiquitin prevents fluid extravasation/capillary leakage in endotoxic shock.

VI. Systemic administration of ubiquitin prevents fluid extravasation/capillary leakage after trauma and hemorrhage.

VII. Systemic administration of ubiquitin prevents development of pulmonary failure in endotoxic shock.

VIII. Systemic administration of ubiquitin inhibits the LPS evoked TNFα release of blood.

These and other aspects of the invention are illustrated in the examples set forth below.

Materials and Methods

1. Healthy Blood Donors and Critically Ill Patients

To study mechanisms of infectious and non-infectious immunodepression in critically ill patients, we examined multiply injured blunt trauma (trauma group) and sepsis patients (sepsis group). We studied blood and/or urine samples from a total of 34 healthy adult blood donors, 20 multiply injured blunt trauma patients (trauma group) and from 24 sepsis patients (sepsis group) from an interdisciplinary intensive care unit. The protocol used was approved by the local ethics committee. All patients and blood donors were Caucasians. The age of the healthy and uninjured blood donors (13 female/21 male) was 31±7 yrs (mean±SD). Blood donors had no signs of infectious diseases four weeks prior to blood collection.

Trauma patients (female/male 8/12) fulfilled the following criteria:
 i) no penetrating injuries
 ii) severity of injury with an injury severity score (ISS) of more than 16 points
 iii) no preexisting chronic illness Trauma patients were assigned an ISS by independent evaluators. Injuries of the various body regions (head and neck, face, thorax, abdomen, extremities, skin) were classified using the Abbreviated Injury Scale (AIS), which ranges from 0 (no injury of the body region) to 6 (fatal injury of the body region) for each body region.

The age of the trauma patients was 39±18 yrs (mean±SD) and the ISS was 27±10 (mean±SD) points (AIS head/neck: 2.1±1.5, AIS face: 0.9±1.5, AIS thorax: 2.6±1.7, AIS abdomen: 0.7±1.4, AIS extremities: 2.2±1.7, AIS skin: 0.2±0.6). Five trauma patients died.

Sepsis patients (female/male: 8/16) fulfilled the Criteria of the American College of Chest Physicians/Society of Critical Care Medicine consensus conference (10 patients for sepsis, 7 patients for severe sepsis and 7 patients for septic shock). The age of the sepsis patients was 52±18 yrs (mean±SD). The source of infection was pneumonia in 17 patients, peritonitis in 6 patients and pancreatitis in one patient. Five sepsis patients with septic shock died. All patients requiring surgical intervention received standard surgical care and postoperative intensive care unit treatment.

2. Animals

All experimental protocols using animals were performed in accordance with the guidelines for the care and use of experimental animals as outlined by the NIH. Cross-bred, farm-raised swine used in these experiments were housed in a facility approved by the American Association for the accreditation of Laboratory Animal Care and were continuously monitored by staff veterinarians for any signs of unnecessary pain or distress. Except for the overnight fast, during which animals were allowed access to water only, food and water were provided ad libitum.

2.1 General Animal Preparation

After an overnight fast, pigs were induced with i.m. ketamine (30 mg/kg)+xylazine (3.5 mg/kg) and anesthetized with a continuous infusion of fentanyl (20 µg/kg/hr), supplemented with ketamine (10 mg/hr) to maintain anesthesia, and mechanically ventilated (Bear MA-2, $FiO_2$ 0.5 PEEP 0) via tracheostomy in the supine position. A self-calibrating flow transducer (Var-Flex, Bicore Monitoring Systems, Allied Technical, Riverside, Calif.) and a balloon tipped esophageal catheter (SmartCath, Bicore) were connected to a pulmonary function monitor (Bicore CP-100). Tidal volume was initially adjusted to a peak inspiratory pressure <20 cm $H_2O$, with respiratory rate adjusted to $PaCO_2$=30–50 mm Hg, then not changed for the remainder of the experiment. Catheters were placed in the femoral artery and internal jugular vein for measurement of systemic arterial pressure and for fluid administration. A multi-lumen, flow-directed fiberoptic pulmonary artery catheter (Swan-Ganz Combo Thermodilution Catheter, Baxter Labs, Irvine, Calif.) was advanced via an introducer sheath (Arrow International, Inc., Reading, Pa.) from the external jugular vein into the pulmonary artery for continuous measurement of filling pressures, $O_2$ saturation, and cardiac output (Vigilance Computer, Baxter Labs). Flow-through pressure transducers were connected to the appropriate catheter ports to eliminate the use of heparin. Body temperature was maintained with a heating blanket. EKG was continuously monitored. During instrumentation, animals received 1 L of Lactated Ringer's. After achieving stable baseline conditions (at least 45 min after instrumentation) and fulfillment of inclusion criteria (leukocyte counts ≦15/nL, Temp. <38° C.) animals were subjected to one of the following experimental procedures, which were chosen to simulate a harmful activation of the immune system.

2.2 Models of a Harmful Activation of the Immune System

To simulate both infectious and non-infectious activation of the immune system, two different animals models were used:

2.2.1 Endotoxic Shock

As a model of an infectious activation of the immune system, animals were subjected to an intravenous endotoxin infusion and ubiquitin (Ub) was administered either before (pre-treatment) or during endotoxin infusion (post treatment).

2.1.1 Pre-treatment with Ubiquitin

After achieving baseline conditions, animals received either an intravenous bolus injection of 0.13 mg Ub/kg body weight (n=3), 1.3 mg Ub/kg body weight (n=6) or placebo (bovine serum albumin (BSA), n=11) in 250 mL 0.9% NaCl within 15 min (time point—15 min). Following the i.v. bolus of either Ub or BSA, endotoxin (lipopolysaccharide (LPS) from *Salmonella abortus equi*) was infused at 0.5 µg/kg body weight/hr for 3 h. Fluid resuscitation with Lactated Ringer's was started when the mean arterial blood pressure reaches 69 mmHg and continued until a mean arterial blood pressure of 70 mmHg was achieved.

2.2.1.2 Post-treatment with Ubiquitin

After achieving baseline conditions, endotoxin (lipopolysaccharide (LPS) from *Salmonella abortus equi*) was infused at 0.5 µg/kg body weight/hr for 3 h (time point 0). At time point +45 min animals received either an intravenous bolus injection of 1.3 mg Ub/kg body weight (n=6) or placebo (bovine serum albumin (BSA), n=8) in 250 mL 0.9% NaCl within 5–10 min. Fluid resuscitation with Lactated Ringer's was started when the mean arterial blood pressure reaches 69 mmHg and continued until a mean arterial blood pressure of 70 mmHg was achieved.

2.2.2 Femur Fracture+Hemorrhage

As a model of a non-infectious activation of the immune system, animals were subjected to trauma and hemorrhage. After baseline data were collected, FiO2 was decreased to 0.21 and a modified captive bolt gun (Model ME, Schermer & Co., Germany) was fired against the femura, which produced complex 2° open fractures of the distal 2/3 of the femura. After fracture, within 2–5 min, the stopcock on the femoral artery catheter was opened so that blood drained into a plastic bag. The stopcock was closed when mean arterial pressure reached a target value of 25 mm Hg. The hemorrhage to achieve the target pressure averaged 800±80 ml in a typical 50 kg animal. The shock period was maintained for 30 min.

After the shock period, $FiO_2$ was increased to 0.5, and animals received either an IV bolus injection of 1.3 mg Ub/kg body weight (n=5) or placebo (bovine serum albumin (BSA), n=5) in 250 mL 0.9% NaCl within 5–10 min, followed by fluid resuscitation with Lactated Ringer's to achieve a mean arterial pressure (MAP) of 70 nunhg. Fluid resuscitation with Lactated Ringer's was started when the mean arterial blood pressure reaches 69 mmHg and continued until a mean arterial blood pressure of 70 mmHg was achieved. This series of experiments was performed blinded, with the physician not knowing if either Ub or BSA was infused.

2.3 Data Collection

The following were monitored continuously online: esophageal pressure, airway pressure, airway flow, core temperature, end tidal $CO_2$, peak inspiratory pressure, heart rate, mean arterial pressure, pulmonary capillary wedge pressure, mixed venous $O_2$ saturation, and cardiac output. Blood gases ($PaO_2$, $PCO_2$, pH, base excess, and arterial $O_2$ saturation), lactate and electrolytes ($Na^+$, $K^+$, $Cl^+$, $Ca^{+2}$, glucose, and osmolarity) were recorded at 15–30-minute intervals on a Nova Stat Profile Ultra (Waltham, Mass.). Complete blood counts (hematocrit, leukocyte count, and platelet count) were determined via arterial blood draw on an Abbott Cell-Dyn 1600 (Abbott Park, Ill.).

3. Blood Collection

Blood was collected in plastic tubes ($NH_4$-heparin-(9 ml) and serum-(9 ml) tube, Sarsted, Germany) along with the routine baseline laboratory work-up in patients and sequentially at defined time points in animals. Whole blood collected in a serum tube was separated and the sera were aliquoted and stored frozen at –70° C. Furthermore, blood from mice (n=3, 25–35 g body weight) was collected in a $NH_4$-heparine tube.

Whole blood collected in a $NH_4$-heparine tube was immediately used for culture experiments and for isolation of PBMNCs.

4. Analytical Methods

4.1 Isolation of Peripheral Blood Mononuclear Cells and Cell Cultures

PBMNCs were isolated by density centrifugation of heparinized blood diluted 1:1 (v/v) in phosphate buffered saline over a Lymphoprep (Nycomed Pharma AS, Norway) density gradient and were used for endotoxin stimulation immediately after isolation. Whole blood mixed 1:3 (v/v) with cell culture medium (RPMI 1640 or $10^5$ PBMNC resuspended in cell culture medium (RPMI 1640 (GibcoBRL, Germany) containing 10% serum were transferred to microtiter plates (Greiner Bio One, Greiner, Germany). Samples were prepared in duplicate. The mixtures were incubated at 37° C. and 5% $CO_2$ with LPS (100 ng/mL; from *Salmonella abortus equi* (Sigma, Germany)). Control mixtures were incubated without LPS. After incubation the supernatants were separated and stored frozen at –20° C. Following endotoxin stimulation PBMNCs were tested for viability by incorporation of 3-(4,5 dimethylthiazol-2-yl)-2,5,diphenyltetrazoliumbromide (MTT, Sigma, Germany).

4.2 Proteins and Antibodies

Ubiquitin was purchased from Sigma (U 6253; Taufkirchen, Germany). Biotinylated ubiquitin (Ub-b) was purchased from Boston Biochemicals (Boston, Mass.). Human recombinant interleukin-10 (I 9276) was purchased from Sigma (Taufkirchen, Germany). Rabbit anti-ubiquitin antiserum (AS) (U5379), ubiquitin-fluorescein conjugate (U5504), goat antiserum to rabbit IgG (R8633) and peroxidase-labeled anti-biotin antibodies were purchased from Sigma (Taufkirchen Germany). Monoclonal mouse anti-ubiquitin antibody (Ub P4D1) and goat polyclonal anti-ubiquitin antibody (Ub N-19) were purchased from Santa Cruz Biotechnology (USA). Peroxidase-linked anti-rabbit and anti-mouse IgG was obtained from Amersham-Pharmacia (Germany).

4.3 Immunoassays

4.3.1 Ubiquitin—human

Quantification of ubiquitin concentrations in human serum und urine specimen was performed with a competitive binding immunoassay, in which ubiquitin-fluorescein conjugate and ubiquitin in the test sample compete for a limited number of binding sites in the anti-ubiquitin antiserum. Two to 4 dilutions of each serum/urine sample were measured in duplicates. In brief, 100 µl of ubiquitin-fluorescein conjugate, 100 µl of the test sample and 100 µl of the rabbit anti-ubiquitin antiserum were transferred to plastic tubes, mixed and incubated for 60 min at room temperature in the dark. After incubation, 1 mL of goat antiserum to rabbit IgG was added to the test tubes, the solution was centrifuged for 15 min at 4° C. and the supernatant was removed. The pellet was resuspended in 2 mL 0.1 N NaOH, 2% SDS and the fluorescence ($\lambda$excitation 485 nm, $\lambda$emission 535 nm) was measured in a Genios-microreader (Tecan, Germany). The ubiquitin concentration in the test sample was calculated from a non-linear regression analysis employing ubiquitin as standard (0–1000 ng/mL). The non-linear regression analysis (one-phase exponential decay) was calculated with the GraphPad Prism program (GraphPad Inc, USA). The correlation coefficients for each standard curve were 0.95–1. The lower detection limit was determined to be 17 ng ubiquitin/mL.

4.3.2 Ubiquitin—porcine

Quantification of ubiquitin serum levels in porcine serum samples was performed using a competitive direct enzyme linked immunosorbent assay (ELISA). Microtiter plates (Nunc, Germany) were coated with anti-ub AS and incubated for 18 h at 4° C. The plates were washed three times with 0.05% tween 20 in phosphate buffered saline and were incubated with blocking buffer (0.5% bovine serum albumin (BSA, Sigma) in phosphate buffered saline) for 1.5 h. After washing three times, 50 µl of the standards or samples were mixed with 50 µl of Ub-b and placed in the plates. Each sample was tested in 4–8 dilutions. Dilutions for the standard curve and the test samples were prepared using blocking buffer.

After incubation for 1.5 h the plates were washed again and a peroxidase-labeled anti-biotin-antibody was added. After incubation for 1.5 h the plates were washed again and 100 µL TMB ELISA solution (Sigma, Germany) was added. After incubation for 20–40 min, the reaction was stopped by addition of 100 µL HCl and optical densities were measured using a micro-ELISA autoreader (µQuant, Bio-Tek Instruments; test filter: 450 nm; reference filter: 540 nm). The ubiquitin concentration in the test sample was calculated from a non-linear regression analysis employing ubiquitin as standard (0–1700 ng/mL). The non-linear regression analysis (one-phase exponential decay) was calculated with the GraphPad Prism program (GraphPad Inc, USA). The correlation coefficients for each standard curve were 0.95–1. The lower detection limit was determined to be 25 ng ubiquitin/mL.

4.4 Cytokines

Quantification of TNFα, IL-6 and IL-8 concentrations in cell cultures and serum samples were performed using commercially available enzyme linked immunosorbent assay (ELISA) kits (human: Millenia Biotech, Bad Nauheim, Germany; porcine and murine: R&D Systems, Wiesbaden, Germany) according to the manufacturer's instructions. The lower detection limits of the ELISAs were 10 pg/mL for human TNFα, 1.2 pg/mL for human IL-6, 3.5 pg/mL for human IL-8, 5 pg/mL for porcine TNFα and 5 pg/mL for murine TNFα.

4.5 Immunoblotting

Following SDS-PAGE serum or urine samples were electrophoretically transferred to a polyvinylidene difluoride membrane (Hybond-P, Amersham-Pharmacia, Freiburg, Germany). After blocking residual binding sites on the membrane with 5% (w/v) non-fat dried milk powder (Milupa, Germany), 0.1% Tween 20 (Sigma, Taufkirchen Germany) in phosphate buffered saline immunoblotting was performed with anti-ubiquitin AS (1:200 (v/v)) and monoclonal Ub P4D1 (1: 500 (v/v)) using a corresponding second horseradish-peroxidase labeled antibody (1:10000 (v/v) and 1:5000 (v/v), respectively; Amersham Biosource, Freibug, Germany). Immunoreactive proteins were visualized with a enhanced chemiluminescence (ECL-Plus) detection system (Amersham Pharmacia, Freiburg, Germamy) using the ImageMaster VDS-CL video system (Amersham Pharmacia, Freiburg, Germany).

4.6 Affinity Chromatography

Anti-ubiquitin affinity chromatography was performed using the rabbit anti-ubiquitin antiserum (Sigma, Taufkirchen, Germany). HiTrap NHS-activated columns (1 mL column (7 mm inner diameter×25 mm column height), Amersham Pharmacia, Germany) were incubated with rabbit anti-ubiquitin antiserum (4 mg/mL in 0.2 M NaHCO$_3$, 0.5 M NaCl, pH 8.3) for 30 min at ambient temperature. After incubation, the column was washed and deactivated with several volumes of 0.5 M ethanolamine, 0.5 M NaCl, pH 8,3 (buffer A), 0.1 M acetate, 0.5 M NaCl, pH 4 (buffer B) and again with buffer A with a flow rate of 1 mL/min. Following 25 min incubation in buffer A at ambient temperature, the colum was washed again and was then equilibrated with RPMI 1640 (Gibco BRL, Germany). Patient serum 1:1 (v/v) in RPMI 1640 was applied to the column and was incubated for 30 min. The run-through was collected and the column was washed with several volumes of RPMI 1640. The column was eluted with a five step pH gradient of each 2 column volumes of 0.2 M glycin at pH 7, pH 6, pH 5, pH 4 and pH 3 with a flow rate of 1 mL/min. Fractions of 1 mL were collected. Immediately after elution, the fractions were neutralized to pH 7.5 and were used in cell culture experiments.

4.7 mRNA Quantification

TNFα mRNA levels in endotoxin stimulated PBMNCs ($10^6$ PBMNC/mL) were quantified using a commercially available colorimetric microplate assay kit (Qantikine mRNA, R&D systems, Wiesbaden, Germany) according to the manufacturer's instructions. The lower detection limit is 3.2 amol TNFα mRNA/mL.

4.8 Other Procedures and Substances

Protein was determined with a protein assay kit (P 5656 Sigma, Germany) employing bovine serum albumin as standard. Protein standards for gel electrophoresis were purchased from Amersham Pharmacia (Germany). Zymosan A (Z 4250) was purchased from Sigma (Taufkirchen Germany). Heat killed *Staphylococcus aureus* (clinical isolates, autoclaved) was kindly provided by Prof. Dr. H. Hof, Institute of Medical Microbiology, University Hospital Mannheim, Germany. Cells were counted with a XR-21 automatic multi-channel hematology cell counter (Sysmex, Norderstadt, Germany).

4.9 Statistics

If not otherwise mentioned, data are expressed as the mean±the standard error of the mean. Spearman correlation coefficient ($r_s$), Student's t-test and one way analysis of variance (ANOVA) for multiple comparisons were calculated with the SPSS for Windows Release 10.0.7 program. A two-tailed $P<0.05$ was considered significant. Standard curves of the assays and dose-related effects of exogenous ubiquitin were analyzed by linear and non-linear regression analysis using the GraphPad Prism program (version 1.0, 1994, GraphPad Software Inc., San Diego, USA).

EXAMPLE 1

Figure 1:
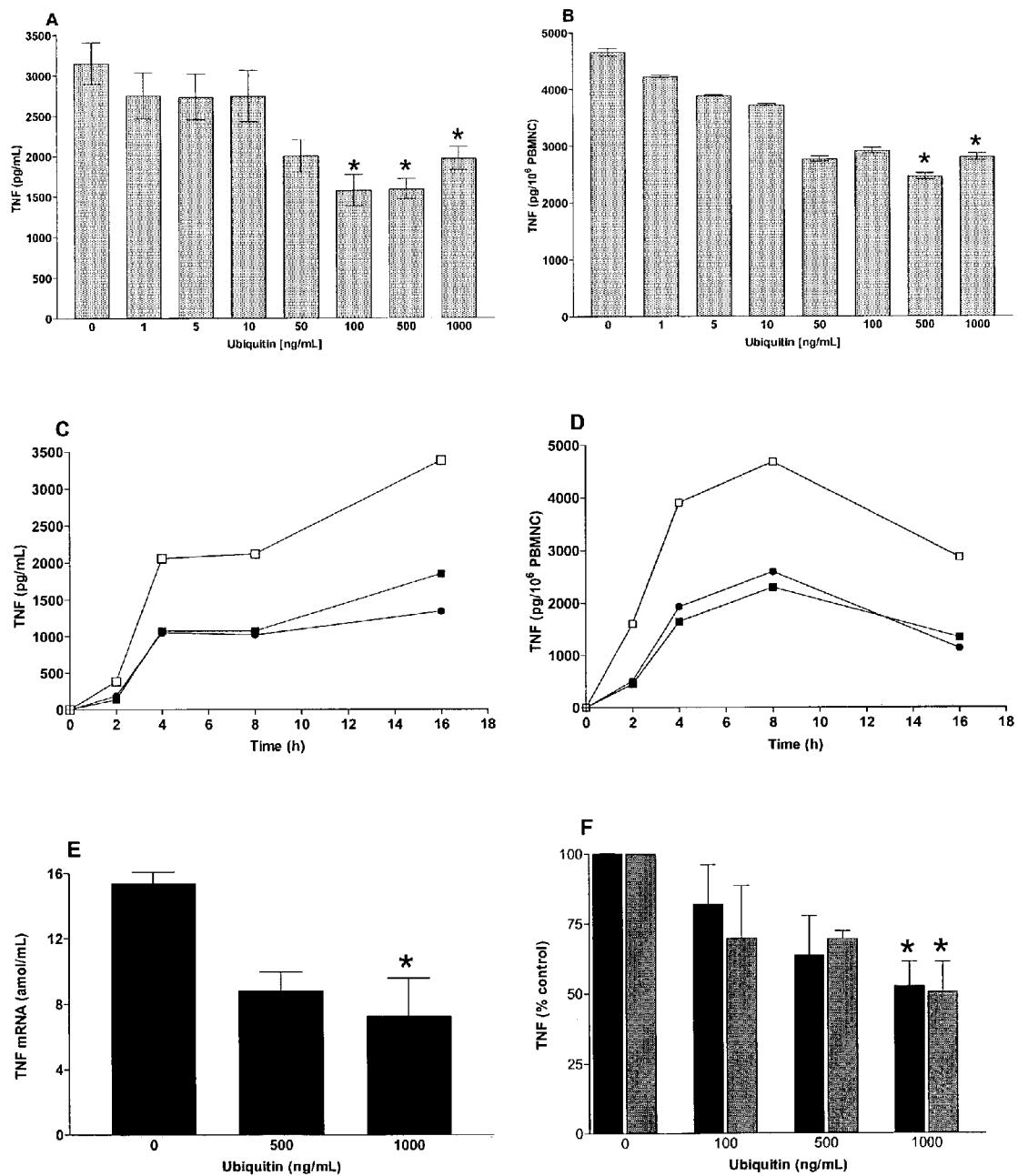
FIGS. 1A–1F demonstrate that exogenous ubiquitin inhibits TNFα secretion of blood and PBMNCs.

Exogenous Ubiquitin Inhibits LPS Induced TNFα Production of Whole Blood and PBMNCs We measured the effect of exogenous ubiquitin on TNFα secretion of human whole blood and PBMNC cultures stimulated with and without LPS. TNFα was not detectable in LPS free whole blood and PBMNC cultures incubated with 0–1 µg/mL exogenous ubiquitin (not shown). As estimated with the MTT assay viability was >90% in all PBMNC cultures (not shown). In whole blood and PBMNC cultures with LPS, exogenous ubiquitin significantly inhibited the TNFα secretion in a dose-dependent manner (correlation coefficients: whole blood $r^2=0.92$; PBMNC $r^2=0.96$) (FIGS. 1A–1F). Maximal inhibition of the TNFα production was found at a concentration of 500 ng/mL exogenous ubiquitin in both whole blood and PBMNC cultures. Kinetics of the LPS stimulated TNFα production of whole blood and PBMNCs showed, that exogenous ubiquitin did not influence the time course of the TNFα secretion within an incubation period of 0–16 h. In order to exclude interference of exogenous ubiquitin with the immunological detection of TNFα in the cell cultures, ubiquitin was added to whole blood and PBMNC cultures (n=8) after 4 h of LPS stimulation. Compared with the control measurements without ubiquitin, in the presence of 500 ng/mL and 1000 ng/mL ubiquitin, the recovery of TNFα was 97±1.7% (mean±SEM) and 96±3% (mean±SEM) respectively. To further confirm the inhibitory effect of exogenously added ubiquitin on LPS stimulated TNFα production, TNFα mRNA levels were quantified. As shown in FIG. 1E, similar to the LPS induced TNFα secretion, exogenous ubiquitin produced a dose-related inhibition of the LPS evoked mRNA expression of human PBMNCs. In line with the findings in human whole blood, exogenous ubiquitin was found to inhibit the LPS induced TNFα response in both murine and porcine whole blood in a dose dependent manner (FIG. 1F).

EXAMPLE 2

Ubiquitin Serum and Urine Concentrations in Healthy Individuals and Critically Ill Patients Determination of ubiquitin levels in serum, plasma and whole blood derived from the same blood specimen revealed equal concentrations in each sample (Table 1), indicating no relevant ubiquitin release during blood clotting or sample preparation. This is corroborated by the finding that ubiquitin serum concentrations in a donors blood specimen were determined to be 84 ng/mL when serum was separated immediately, 90 ng/mL when serum was separated 1 h after collecting the blood in a serum tube and 90 ng/mL after 4 h, respectively.

TABLE 1

Comparison of ubiquitin concentrations in serum, plasma and whole blood

|  | serum | plasma | whole blood |
| --- | --- | --- | --- |
| patient #1: | 338 | 293 | 322 |
| patient #2: | 256 | 247 | 264 |
| Healthy donor | <17 | <17 | <17 |

Patient #1: male, 75 yrs., septic shock.
Patient #2: male, 44 years, trauma day 0, ISS 29.
Healthy donor: male, 31 years.

Ubiquitin was detectable in 27 of the 35 serum samples from healthy blood donors, in all serum samples from multiply injured patients on day 0 and 1 after trauma and in all serum samples from sepsis patients. In healthy individuals ubiquitin serum concentrations were determined to be 58±48 ng/mL (mean±SD). Compared with healthy individuals, the ubiquitin serum concentrations were found to be 6-fold elevated in multiply injured patients (n=23) on day 0 after trauma (359±177 ng/mL (mean±SD)) as well as in 24 sepsis patients (327±203 ng/mL (mean±SD)) (FIG. 2A). Furthermore, we measured ubiquitin concentrations in urine specimens. Similar to the findings in serum specimen, the ubiquitin urine concentrations were found to be in the same range of magnitude with an ubiquitin urine concentration of 41±22 ng/mL (mean±SD) in healthy volunteers and a 4.5-fold increased ubiquitin urine concentration (180±166 ng/mL (mean±SD)) in sepsis patients.

Figure 2:
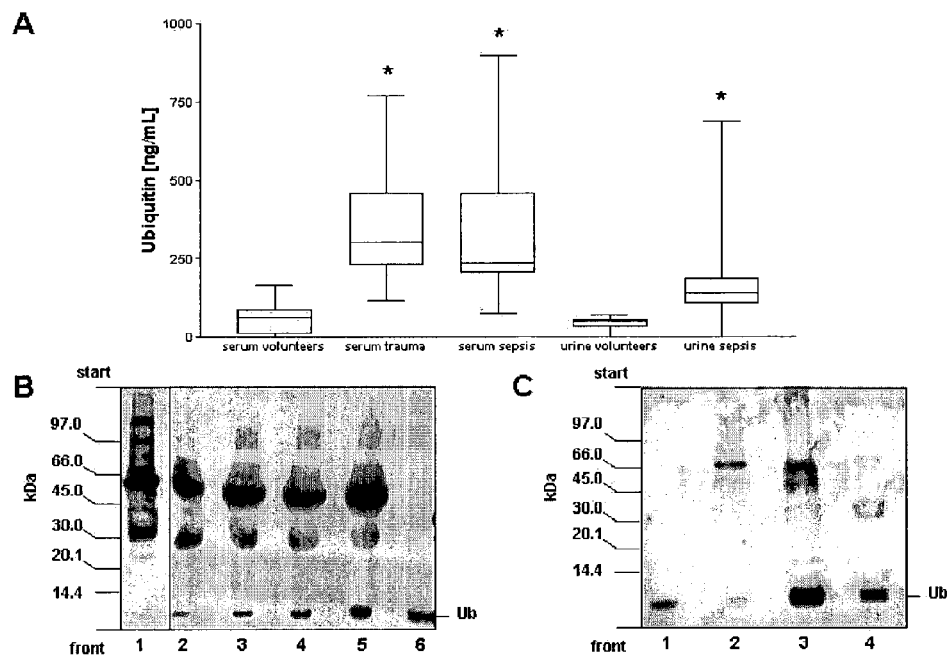
FIGS. 2A–C show levels of ubiquitin in serum and urine.

In addition, we performed immunoblot analysis of patients and healthy donors serum and urine specimen. As determined from control experiments employing ubiquitin as a standard, the detection limit was 1 ng ubiquitin using the anti-ubiquitin AS and 20 ng ubiquitin using the monoclonal UbP4D1 (not shown). Employing both antibodies, patterns of detectable ubiquitin immunoreactive proteins were found to be identical. As shown in FIG. 2, no or only a faint band corresponding to free ubiquitin was detectable in healthy donor samples (FIG. 2B—lane 1; FIG. 2C lane 2), whereas patient serum and urine samples contained a strong band corresponding to free ubiquitin (FIG. 2B/C). Although unspecific binding can not be excluded for each of the numerous high molecular weight bands visualized using both the anti-ubiquitin AS and the monoclonal UbP4D1, obvious differences between patient and healthy donor serum samples were not detectable except for free endogenous ubiquitin.

EXAMPLE 3

Figure 3:
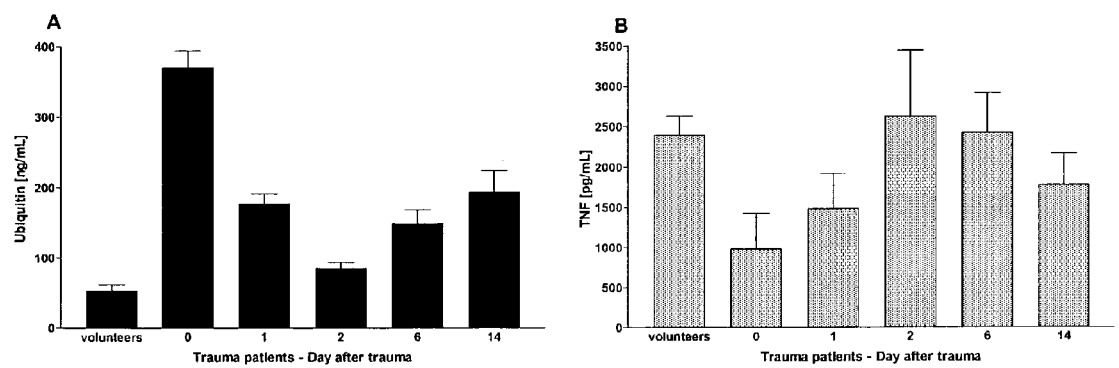
FIGS. 3A–B show a comparison of ubiquitin serum levels with LPS stimulated whole blood TNFα production and neutralization of the inhibitory activity for TNFα production in patients' serum with anti-ubiquitin Ab.

Comparison of Ubiquitin Serum Concentrations with the LPS Induced Whole Blood TNFα Production in Healthy Volunteers and Critically Ill Patients Because ubiquitin serum levels in multiply injured blunt trauma patients were determined to be in the same range of magnitude as determined for the maximal inhibitory activity of exogenous ubiquitin on LPS stimulated TNFα production, we compared ubiquitin serum concentrations with the whole blood TNFα response to LPS in healthy individuals and trauma patients. As shown in FIGS. 3A–B, high ubiquitin serum concentrations are significantly associated with low TNFα concentrations in LPS stimulated whole blood from healthy donors and severely injured patients (n=62, $r_s$=−0.263; P=0.018). In severely injured trauma patients, the ubiquitin serum concentrations on day 0–14 resemble a mirror image of the LPS induced whole blood TNFα production.

EXAMPLE 4

Anti-ubiquitin Antibodies Neutralize the Inhibitory Activity for TNFα Production in Patients' Serum Trauma and sepsis patients' serum is known to mediate immunosuppression and to depress the TNFα producing capacity of volunteers whole blood and PBMNCs. To address the involvement of ubiquitin in this context, we tested the effect of anti-ubiquitin antibodies in whole blood and PBMNC cultures incubated with and without patient serum (FIGS. 4A–4D). In a first series of cell culture experiments, we examined the potential neutralizing effect of anti-ubiquitin antibodies (Ab) on the inhibitory activity of ubiquitin on the LPS induced TNFα secretion. Anti-ubiquitin antiserum was found to neutralize the effect of ubiquitin dose dependent at a dilution of 1:100 and 1:10 without effects on whole blood and PBMNCs cultured in the absence of exogenous ubiquitin. Moreover, the tested monoclonal (Ub (P4D1) diluted 1:1000) and polyclonal anti-ubiquitin Ab (Ub (N-19) diluted 1:1000) neutralized the inhibitory effect of exogenous ubiquitin on the LPS stimulated TNFα release in whole blood and PBMNC cultures. None of these Ab affected the TNFα secretion of cell cultures without exogenous ubiquitin. To further exclude unspecific stimulation induced by immune complexes, the LPS induced TNFα secretion of whole blood and PBMNCs was tested in co-cultures with exogenous human recombinant interleukin-10 (IL-10) and anti-ubiquitin antibodies. The anti-ubiquitin antibodies did not influence the IL-10 induced inhibition of the LPS stimulated TNFα secretion (not shown).

In the second series of experiments, whole blood and PBMNCs from healthy donors were cultured in the presence of trauma (FIG. 4C) and sepsis (FIG. 4D) patient serum and the effect of the anti-ubiquitin antibodies was examined. As expected, trauma patient serum (mean ubiquitin level: 330±99 (SD) ng/mL) reduced LPS stimulated TNFα secretion to 40–50% (FIG. 4C). Addition of anti-ubiquitin antiserum, mono- and polyclonal antibodies neutralized the inhibitory effect of trauma patients serum on whole blood and PBMNCs.

Incubating whole blood and PBMNCs in the presence of sepsis patient serum (mean ubiquitin level: 393±179 (SD)

ng/mL) inhibited the LPS induced TNFα secretion to 30% of the TNFα secretion in the presence of healthy volunteers serum (FIG. 4D). Similar to trauma patient serum, in PBMNC cultures, the inhibition induced by sepsis patient serum was neutralized by anti-ubiquitin antiserum dose-dependently. Compared to trauma patient serum, the neutralizing effects of UbP4D1 and UbN19 were attenuated on PBMNCs incubated with sepsis patient serum. In contrast to PBMNC cultures, the neutralizing effect of anti-ubiquitin AS on the inhibition induced by sepsis patient serum on LPS induced whole blood TNFα production was diminished. Furthermore, the neutralizing effects of UbP4D1 and UbN19 detected in PBMNC cultures were abolished in whole blood cultures incubated in the presence of sepsis patient serum.

EXAMPLE 5

Endogenous Ubiquitin Regulates the Inhibitory Activity for TNFα Production in Patient Serum To obtain direct evidence for the immunomodulatory functions of extracellular ubiquitin, we used anti-ubiquitin affinity chromatography for the depletion and fractionation of endogenous ubiquitin from trauma patient serum. As shown in FIGS. 5A–B, in the unadsorped fraction (run-through) the inhibitory activity for LPS induced TNFα secretion was abolished. In line with the biological activity, immunoblot analysis of the run-through showed, that free endogenous ubiquitin was removed from patient serum. Elution of bound proteins from the anti-ubiquitin column was performed by acidification. Inhibitory activity for LPS induced TNFα secretion was found in the eluted fractions, with a maximal inhibitory effect of the fractions at pH 4. The inhibitory activity measured in fraction 4 was similar to the effect of patient serum immunoblotting of the fractions containing the maximal inhibitory activity showed a single band corresponding to free ubiquitin, whereas the high molecular weight bands were detectable in the unadsorped fractions.

EXAMPLE 6

Figure 6:
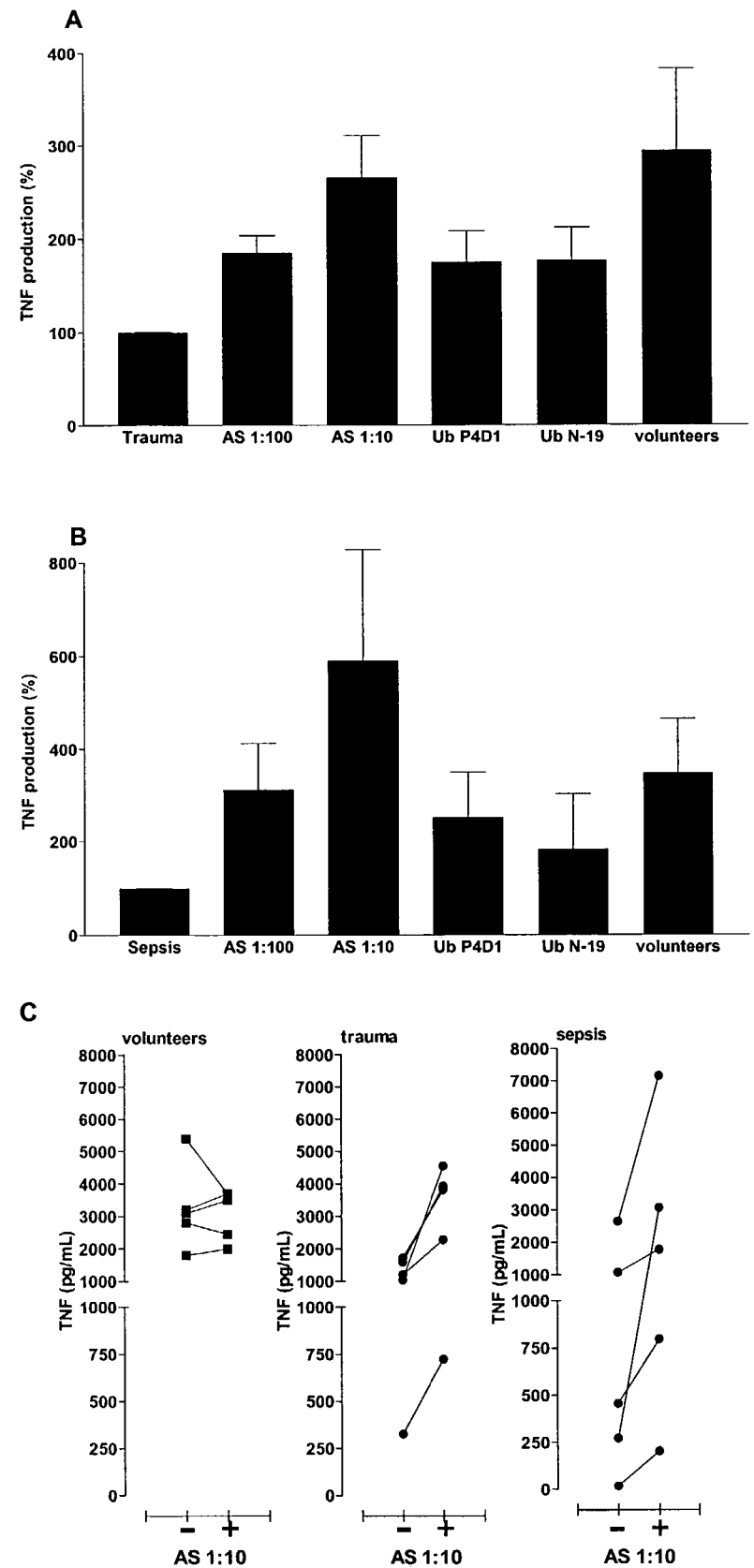

Anti-ubiquitin Antibodies Restore Reduced TNFα Producing Capacities in Trauma and Sepsis Patient Blood We further examined whether neutralization of endogenous ubiquitin in whole blood from critically ill patients normalizes the reduced TNFα producing capacities (FIG. 6).

In healthy donors blood anti-ubiquitin antibodies did not influence the TNFα secretion upon LPS stimulation. In contrast, in every trauma patient's blood (n=5) anti-ubiquitin antiserum increases the TNFα secretion dose dependently 2–3 fold. The increase in TNFα secretion in cultures incubated in the presence of Ub P4D1 and Ub N-19 (1.5–2-fold increase) was lower, but constantly detectable. After neutralization of endogenous ubiquitin in trauma patient blood, mean TNFα secretion reaches the level of uninjured donors. In sepsis patient blood, ubiquitin-antibodies were capable to normalize the reduced LPS stimulated TNFα secretion either. Again, neutralizing ubiquitin increases LPS induced TNFα secretion in every blood sample tested. Compared to trauma patient blood, in sepsis patients the increase in TNFα secretion induced by anti-ubiquitin antiserum (5–6-fold), Ub P4D1 Ab (2–3fold) and Ub N-19 Ab (2-fold) was higher.

This data demonstrates that anti-ubiquitin antibodies restore reduced TNFα producing capacities in trauma and sepsis patient blood.

Taken together, the in vitro results described above demonstrate for the first time that extracellular ubiquitin acts as a cytokine-like protein with anti-inflammatory properties and indicate that extracellular ubiquitin is involved in the regulation of immunosuppression in critical illness. To explore the in vivo effects of ubiquitin, two studies were designed in swine who were anesthetized, mechanically ventilated ($FiO_2$=0.5, PEEP=5 cm $H_2O$), and instrumented for hemodynamic monitoring.

EXAMPLE 7

Ubiquitin Prevents Death After an Otherwise Lethal Endotoxic Challenge

Based on the in vitro findings detailed above, we hypothesized that administration of ubiquitin has anti-inflammatory effects in vivo, and therefore, is beneficial in conditions accompanied by a harmful activation of the immune system, e.g. endotoxic shock.

To demonstrate its in vivo action as an anti-inflammatory immunomodulator ubiquitin was intravenously administered immediately before (LPS/pre-treatment) or 45 min after (LPS/post-treatment) an i.v. infusion of endotoxin for 3 hr. As shown in FIG. 7, in the control group (BSA) mortality was 50% within 3 hrs. In contrast, none of the animals of the ubiquitin pre- or post-treatment group died within the observation period (p=0.013 vs. BSA).

EXAMPLE 8

Ubiquitin Prevents Fluid Extravasation/capillary Leakage and Erythema Formation in Endotoxic Shock The differences in mortality between the BSA and the pre- and post-treatment groups were accompanied by a significant reduction of fluid requirement by ubiquitin, which was even more pronounced in the pre-treatment group (FIGS. 8 and 9). Despite excessive fluid administration in the BSA group (86±57 mL/kg body weight), a MAP of >70 mmHg could not be maintained. In contrast, in both treatment groups, a MAP of >70 mmHg was achieved by administration of 10±10 mL/kg body weight (pre-treatment) and 32±13 mL/kg body weight (post-treatment) (both p<0.05 vs. BSA; FIG. 9).

Coincident with the reduction of fluid requirement by ubiquitin was the finding that all BSA animals developed general and pulmonary edema and bright erythema, whereas ubiquitin pretreatment obviously diminished its development (FIG. 10).

EXAMPLE 9

Ubiquitin Prevents Development of Pulmonary Failure in Endotoxic Shock

In addition to reduction of fluid requirement by ubiquitin, pre-treatment with ubiquitin was found to prevent development of pulmonary failure in endotoxic shock (FIG. 11A). Endotoxin infusion produced development of fulminant pulmonary failure (baseline $PaO_2$: 262±11 mmHg (mean±SEM; Horovitz-ratio: 523); $PaO_2$ at t=180 min: 52.5±6.6 mmHg (mean±SEM; Horovitz-ratio: 105) in BSA animals. BSA animals fulfilled criteria for pulmonary failure (Horovitz ratio <200 mmHg) at t=150 min (Horovitz-ratio: 153). Animals of the ubiquitin pre-treatment group showed only a slight decrease of $PaO_2$ (baseline $PaO_2$: 274±49 mmHg (mean±SEM; Horovitz-ratio: 548); $PaO_2$ at t=180 min: 203±70 mmHg (mean±SEM; Horovitz-ratio: 407). Compared with BSA animals, post-treatment with ubiquitin attenuated the decrease of $PaO_2$ (baseline $PaO_2$: 293±26 mmHg (mean±SEM; Horovitz-ratio: 587); $PaO_2$ at t=180 min: 108±25 mmHg (mean±SEM; Horovitz-ratio: 216).

EXAMPLE 10

Ubiquitin Prevents Fluid Extravasation/capillary Leakage After Trauma/hemorrhage Similar to the findings in endotoxic shock, ubiquitin significantly reduced fluid requirement when administered as an initial i.v. bolus of 1.3 mg ubiquitin/kg body weight followed by fluid resuscitation with Lactated Ringer's after bilateral femur fracture and hemorrhage (non-infectious activation of the immune system; FIG. 11B). BSA animals required 218±36 mL fluid/kg body weight (mean±SEM) to maintain MAP >70 mmHg, whereas ubiquitin animals required only 87±22 mL fluid/kg body weight (mean±SEM; p<0.05 vs. BSA).

Example 11

In-vivo Administration of Ubiquitin Inhibits Endotoxin Evoked TNFα Release in Whole Blood In accordance with the in vitro ability of ubiquitin to inhibit endotoxin induced TNFα secretion of whole blood and peripheral blood mononuclear cells, in vivo administration of 1.3 mg ubiquitin/kg body weight significantly inhibited the TNFα response of whole blood to endotoxin (FIG. 12). Compared with whole blood drawn at t=−15 min (baseline), TNFα production after IV ubiquitin administration (t=0 min) was significantly reduced in whole blood stimulated with 100 ng/mL and 1000 ng/mL LPS and gradually approached baseline levels thereafter.

EXAMPLE 12

Intravenous Administration of Ubiquitin has no Major Side Effects

Intravenous bolus injection of 0.13 mg Ub/kg body weight or 1.3 mg Ub/kg body weight to animals of the pre- and post-treatment groups showed no notable effects directly related to the ubiquitin infusion on any of the measured physiological parameters. To further exclude adverse effects, 1.3 mg ubiquitin/kg body weight was intravenously administered followed by a 3 hr observation period without any further intervention (control group). Baseline ubiquitin serum levels (t=−15 min) were determined to be 362±182 ng/mL (n=9; mean±SEM). I.v. injection of 1.3 mg ubiquitin/kg body weight produced an initial (t=0 min) serum concentration of 12.4±4.3 μg ubiquitin/mL (n=6; mean±SD). Kinetics of ubiquitin serum levels followed a single-phase exponential decay ($r^2$=0.98) and were found to be identical in control animals (n=3) and in animals of the pre-treatment group (n=3) (FIG. 13). As shown in the insert to FIG. 13, measurement of ubiquitin serum concentrations in animals of the BSA group (n=3) showed a 2-fold increase of endogenous ubiquitin with peak levels at t=45 min after infusion of endotoxin.

Despite a slight increase of pulmonary artery pressure and leukocyte counts, ubiquitin had no effects on any other of the physiological parameters measured (Table 2). None of the animals required fluid administration within the observation period.

TABLE 2

| Time | HR (beats/mm) Mean ± SEM | MAP (mmHg) mean ± SEM | CVP (mmHg) mean ± SEM | PAP (mmHg) mean ± SEM | PCWB (mmHg) Mean ± SEM | CO (L/min) mean ± SEM |
|---|---|---|---|---|---|---|
| −15 | 58.7 ± 10.3 | 77.7 ± 0.7 | 1.0 ± 2.5 | 21.3 ± 3.8 | 13.0 ± 3.6 | 6.5 ± 0.5 |
| 0 | 58.3 ± 11.1 | 82.0 ± 2.3 | 0.7 ± 1.7 | 20.7 ± 4.7 | 12.3 ± 3.8 | 5.9 ± 0.2 |
| 30 | 49.3 ± 7.1 | 80.0 ± 1.0 | 1.7 ± 3.2 | 28.3 ± 3.2 | 14.7 ± 8.2 | 6.4 ± 1.4 |
| 45 | 53.3 ± 12.8 | 76.7 ± 2.8 | −0.3 ± 2.1 | 25.7 ± 4.2 | 12.0 ± 7.0 | 7.1 ± 1.1 |
| 60 | 51.3 ± 12.6 | 76.7 ± 1.8 | 0.0 ± 1.5 | 21.7 ± 4.8 | 9.7 ± 5.2 | 7.1 ± 0.8 |
| 90 | 47.3 ± 12.7 | 76.3 ± 1.8 | 0.3 ± 1.3 | 18.0 ± 4.5 | 9.5 ± 2.5 | 7.2 ± 0.5 |
| 120 | 44.3 ± 11.9 | 78.3 ± 1.2 | 0.3 ± 2.4 | 17.0 ± 3.1 | 10.0 ± 2.0 | 7.2 ± 1.4 |
| 150 | 43.0 ± 12.5 | 78.0 ± 3.5 | −1.7 ± 1.2 | 16.7 ± 2.9 | 9.5 ± 0.5 | 6.3 ± 0.8 |
| 180 | 39.0 ± 8.0 | 80.0 ± 3.5 | −1.0 ± 0.6 | 16.3 ± 3.5 | 9.0 ± 1.0 | 7.3 ± 0.8 |

| Time | $PaO_2$ (mmHg) Mean ± SEM | $PaCO_2$ (mmHg) mean ± SEM | $SvO_2$ (%) mean ± SEM | Na (mM) Mean ± SEM | K (mM) Mean ± SEM | $Ca^{2+}$ (mM) mean ± SEM |
|---|---|---|---|---|---|---|
| −15 | 272.4 ± 40.7 | 34.4 ± 3.1 | 88.5 ± 0.5 | 147.7 ± 2.0 | 2.9 ± 0.1 | 0.84 ± 0.03 |
| 0 | 238.6 ± 56.5 | 33.6 ± 3.4 | 89.0 ± 1.0 | 148.7 ± 2.4 | 2.9 ± 0.2 | 0.83 ± 0.05 |
| 30 | 291.0 ± 8.5 | 37.4 ± 4.1 | 87.0 ± 0.0 | 146.7 ± 2.3 | 3.1 ± 0.2 | 0.91 ± 0.10 |
| 45 | 264.2 ± 17.0 | 33.3 ± 3.1 | 87.0 ± 3.0 | 145.7 ± 2.7 | 3.3 ± 0.1 | 1.04 ± 0.12 |
| 60 | 273.9 ± 13.1 | 32.7 ± 2.4 | 82.5 ± 3.5 | 147.3 ± 1.5 | 3.1 ± 0.2 | 0.86 ± 0.07 |
| 90 | 271.7 ± 18.4 | 32.3 ± 5.5 | 83.0 ± 2.0 | 148.0 ± 2.3 | 3.1 ± 0.1 | 0.85 ± 0.10 |
| 120 | 257.7 ± 27.8 | 34.1 ± 5.0 | 86.0 ± 11.0 | 150.0 ± 2.6 | 2.7 ± 0.1 | 0.73 ± 0.08 |
| 150 | 265.7 ± 22.8 | 30.1 ± 2.1 | 81.0 ± 6.0 | 146.3 ± 2.9 | 3.5 ± 0.3 | 1.09 ± 0.17 |
| 180 | 264.7 ± 16.7 | 37.2 ± 5.3 | 78.5 ± 4.5 | 147.3 ± 2.0 | 3.4 ± 0.1 | 0.98 ± 0.03 |

| Time | Glucose (mg/dL) Mean ± SEM | Lactate (mM) mean ± SEM | Hb (mg/dL) mean ± SEM | Hct (%) mean ± SEM | WBC (/nL) Mean ± SEM | PLT (/nL) mean ± SEM |
|---|---|---|---|---|---|---|
| −15 | 119.0 ± 3.0 | 0.7 ± 0.4 | 7.9 ± 0.3 | 24.3 ± 1.7 | 6.3 ± 0.7 | 269 ± 6 |
| 0 | 128.3 ± 12.9 | 0.5 ± 0.2 | 7.6 ± 0.4 | 23.3 ± 0.7 | 6.4 ± 0.8 | 256 ± 13 |
| 30 | 136.3 ± 35.9 | 0.6 ± 0.1 | 7.5 ± 0.3 | 25.0 ± 3.2 | 6.4 ± 0.8 | 253 ± 10 |
| 45 | 130.7 ± 30.2 | 0.7 ± 0.1 | 7.9 ± 0.4 | 25.7 ± 2.7 | 7.3 ± 0.7 | 250 ± 13 |

TABLE 2-continued

| 60  | 108.7 ± 13.6 | 0.6 ± 0.2 | 7.9 ± 0.5 | 23.0 ± 1.5 | 7.4 ± 1.0  | 246 ± 10 |
| 90  | 106.5 ± 1.5  | 0.7 ± 0.1 | 7.7 ± 0.4 | 23.7 ± 1.2 | 8.0 ± 1.4  | 228 ± 12 |
| 120 | 80.0 ± 8.0   | 0.7 ± 0.1 | 7.8 ± 0.7 | 20.7 ± 0.9 | 9.9 ± 0.5  | 237 ± 16 |
| 150 | 86.0 ± 18.0  | 1.1 ± 0.2 | 8.3 ± 0.7 | 28.0 ± 3.2 | 11.1 ± 0.4 | 224 ± 19 |
| 180 | 75.0 ± 12.0  | 1.0 ± 0.1 | 8.3 ± 0.7 | 26.7 ± 1.5 | 12.2 ± 0.4 | 222 ± 13 |

The results of Examples 1–12 show that exogenous ubiquitin inhibits the LPS induced TNFα response of whole blood and PBMNCs in a dose-dependent manner.

Based on the finding that inhibition of the TNFα response of human PBMNCs was detectable at a concentration (0.5 μg/mL (58 nM)) 40–200-fold below the concentrations required for growth suppression (20 μg/mL (2 μM)) [16] and induction of apoptosis (100 μg/mL (12 μM)) [10] of KT-3 and HL-60 cells, the immunomodulatory action of exogenous ubiquitin appears to be of high specificity.

In contrast to the present results is the finding that exogenous ubiquitin augments the LPS-stimulated (1 μg/mL) TNFα secretion of the murine macrophage cell line Raw 246.7 [15]. In addition to the difference that this effect required a 20-fold higher concentration of exogenous ubiquitin in the cell cultures [15], our own preliminary studies using the murine macrophage cell line J774 showed neither inhibitory nor synergistically effects of exogenous ubiquitin on TNFα secretion to LPS (Krehmeier U., and M. Majetschak, unpublished observation). In connection with the finding that exogenous ubiquitin inhibits the LPS evoked TNFα response of murine and porcine whole blood similar to human blood, cell line specific mechanisms may explain these differences.

However, the findings in murine macrophage cell lines indicate, that neutralization of LPS by exogenous ubiquitin, e.g. by LPS binding, is not accountable for the inhibitory effects in human PBMNCs. Although exogenous ubiquitin at 100 μg/mL was found to inhibit proliferation in several hematopoetic cell lines after 48 h of incubation, the inhibitory effect, as measured with the MTT assay, was marginal on MOLT-4 cells and human PBMNCs [10]. Therefore, our finding that ubiquitin did not effect viability of human PBMNCs after 4 h of incubation is not contradictory.

Because indirect evidence has been obtained for the transport of exogenous ubiquitin into the cell, metabolization via ubiquitination to target proteins and degradation by the proteasome system [10], a similar mechanism could possibly explain the effects in human PBMNCs. Human PBMNCs have been described as containing 50 ng free ubiquitin per cells from 1 mL of blood [26]. As estimated from these data, the amount of free ubiquitin approximates 7 fg/cell. In the examples set forth above, the amount of exogenous ubiquitin per PBMNC supplied in the cell cultures was 150–300-fold higher. Although the mechanism of ubiquitin transport into intact cells is unknown, the high extracellular ubiquitin content could possibly explain a significant increase of the intracellular ubiquitin concentration, if even a small proportion of exogenously supplied ubiquitin is transported into the PBMNCs.

The ubiquitin serum concentrations determined in healthy volunteers are in agreement with the normal range determined by others [7, 8, 26]. Compared with healthy volunteers, ubiquitin concentrations were found to be significantly 5–7-fold increased in serum from both trauma and sepsis patients, and to be 4.5-fold increased in sepsis patient urine. Surprisingly, patient ubiquitin serum concentrations were on a level with the ubiquitin concentration required for inhibition of the PBMNCs TNFα response to LPS.

In contrast to IL-10, IL-4 and TGFP serum levels in trauma patients [25], we found high ubiquitin serum levels to be significantly associated with a low LPS stimulated TNFα secretion into trauma patients' blood.

Although comparison of the inhibitory serum activity measured in trauma and sepsis patient serum (50% inhibition by 30% (v/v) serum with a mean ubiquitin concentration of 350 ng/mL) with the dose dependent effect of exogenous ubiquitin on LPS evoked TNFα production showed that the inhibitory activity can not be explained exclusively by ubiquitin, anti-ubiquitin antibodies were able to neutralize the inhibitory activity of trauma patient serum on PBMNCs and whole blood from healthy donors. Furthermore, neutralization of ubiquitin with anti-ubiquitin-AS, mono- and polyclonal antibodies in trauma patient blood restored the TNFα response to LPS to a level comparable with healthy volunteers. In addition, direct evidence of an involvement of ubiquitin in immunoregulation was provided by the finding that trauma patient serum lost the inhibitory activity after ubiquitin depletion and that endogenous ubiquitin appears to be inhibitory for TNFα secretion of LPS stimulated human blood.

With regard to the higher molecular weight bands visualized in serum by immunoblotting using both anti-ubiquitin AS and monoclonal UbP4D1 Ab, affinity chromatography showed that they were not bound to immobilized anti-ubiquitin-AS, whereas free ubiquitin was retained. Besides low affinity or competitive binding [27], where sample proteins compete with binding sites and are displaced by high affinity bound free ubiquitin, unspecific binding in immunoblotting could explain that ubiquitin immunoreactive proteins are detectable in the unadsorbed fractions. However, the finding that the unadsorbed fractions exert no effect on the LPS evoked TNFα response indicate that these ubiquitin immunoreactive proteins are not related to the inhibitory activity, which can be neutralized by anti-ubiquitin antibodies.

Although anti-ubiquitin antiserum was able to neutralize the inhibition induced by sepsis patient serum on PBMNCs, mono- and polyclonal anti-ubiquitin antibodies showed a decreased neutralizing activity on PBMNCs and hardly any capacity in neutralizing the inhibitory effect of sepsis patient serum on whole blood cultures. Nevertheless, all anti-ubiquitin antibodies tested were able to revert reduced LPS stimulated TNFα secretion in sepsis patient blood, with a slightly higher neutralizing capacity in sepsis than in trauma patient blood. The finding that anti-ubiquitin-AS was more effective to revert a depressed TNFα response to LPS than monoclonal UbP4D1 in both trauma and sepsis patient serum and blood is in agreement with the higher sensitivity of anti-ubiquitin AS to detect free ubiquitin by immunoblotting.

Although the origin of extracellular ubiquitin in critically ill patients remains to be determined, secretion of intracellularly synthesized ubiquitin [10] as well as liberation of intracellular ubiquitin by tissue damage are possible explanations. In particular, the latter hypothesis could explain the early appearance of reduced leukocyte function and availability of inhibitory serum activity for TNFα production in trauma patients, which have been shown to be detectable 94±89 min (minimum: 25 min) after the traumatic event [29]. In this model, extracellular ubiquitin could possibly serve as a reservoir for immediate ubiquitin-dependent regulatory immune functions where the cell is not capable of maintaining a sufficient cytosolic level.

In a model of septic shock, extracellular ubiquitin attenuates malignant hostdefense changes and prevents clinical sequelae evoked by LPS, which suggests a potential physiologic role during exaggerated activation of the immune system after trauma, sepsis, or other harmful inflammatory situations. Although pre-treatment with ubiquitin was more effective than post-treatment, the results indicate the therapeutic potential of ubiquitin as a protein therapeutic to prevent and treat a harmful activation of the immune system. In line with the results from the septic shock model, in a model of traumatic shock, exogenous ubiquitin administered following trauma/hemorrhage dramatically reduces fluid resuscitation requirements, emphasizing its therapeutic potential for treatment of immunodysfunction in inflammatory responses of infectious and non-infectious origin.

In summary, the results presented in the present application support the conclusion that extracellular ubiquitin has a physiologic role as a mediator or modulator of malignant inflammatory responses, and modifier of leukocyte function and indicate ubiquitin as a therapeutic for treatment and prevention of a broad spectrum of pathological conditions associated with exaggerated host defense mechanisms.

References cited herein are listed below for convenience and are hereby incorporated by reference.

1. Goldstein, G. M., U. Scheid, D. H. Hammerling, D. H. Schlesinger, H. D. Niall and E. A. Boyse. Isolation of a polypeptide that has lymphocyte-differentiating properties and is probably represented universally in living cells. Proc. Natl. Acad. Sci. USA. 1975;72:11–5.
2. Ozkaynak, E., D. Finley, and A. Varshavsky. The yeast ubiquitin gene: head-to-tail repeats encoding a polyubiquitin precursor protein. Nature. 1984:312:663–6.
3. Hershko, A. and A. Ciechanover. The ubiquitin system. Annu Rev Biochem. 1998;67:425–79
4. Pickart, C., M. Ubiquitin enters the new millennium. Meeting review. Molecular Cell. 2001;8:499–504.
5. Ben-Neriah, Y. Regulatory functions of ubiquitination in the immune system. Nat. Immunol. 2002;1:20–6.
6. Seufert, W. and S. Jentsch. In vivo function of the proteasome in the ubiquitin pathway. EMBO J. 1992; 11:3077–80.
7. Asseman, C., V. Pancre, A. Delanoye, A. Capron, and C. Auriault. A radioimmunoassay for the quantification of human ubiquitin in biological fluids: application to parasitic and allergic diseases J Immunol Methods. 1994;173:93–101.
8. Takagi, M., M. Yamauchi, G. Toda, K. Takada, T. Hirakawa, and K. Ohkawa. Serum ubiquitin levels in patients with alcoholic liver disease. Alcohol. Clin. Exp. Res. 1999;23: 76–80.
9. Akarsu, E., I. Pirim, I. Capoglu, O. Deni, G. Akcay, and N. Ulnuvar. Relationship between electroneurographic changes and serum ubiquitin levels in patients with type 2 diabetes. Diabetes Care. 2001;24:100–3
10. Daino, H., I. Matsumura, K. Takada, et al. Induction of apoptosis by extracellular ubiquitin in human hematopoietic cells: possible involvement of STAT3 degradation by proteasome pathway in interleukin 6-dependent hematopoietic cells. Blood. 2000;95:2577–85
11. Okada, M., S. Miyazaki, and Y. Hirasawa. Increase in plasma concentrations of ubiquitin in dialysis patients: possible involvement in beta 2-microglobulin amyloidosis. Clin. Chim. Acta. 1993;5:135–144.
12. Akarsu, E., I. Pirim, N.Y. Selcuk, H. Z. Tombul, and R. Cetinkaya. Relation between serum ubiquitin levels and KTIV in chronic hemodialysis patients. Nephron. 2001;88:280–2
13. Pancre, V., R. J. Pierce, F. Fournier, et al. Effect of ubiquitin on platelet functions: possible identity with platelet activity suppressive lymphokine (PASL). Eur. J. Immunol. 1991; 21:2735–41.
14. Nakamura, M., R. M. Xavier, and Y. Tanigawa. Ubiquitin-like moiety of the monoclonal nonspecific suppressor factor beta is responsible for its activity. J. Immunol. 1996;156: 532–8
15. Nabika, T., M. Terashima, I. Momose, Y. Hosokawa, N. Nagasue, and Y. Tanigawa. Synergistic effect of ubiquitin on lipopolysaccharide-induced TNF alpha production in murine macrophage cell line Raw 264.7. Biochim. Biophys. Acta. 1999;1450:25–34.
16. Daino, H., H. Shibayama, T. Machii, and Kitani, T. Extracellular ubiquitin regulates the growth of human hematopoietic cell. Biochem. Biophys. Res. Commun. 1996;223:226–228.
17. Docke, W., D., F. Randow, U. Syrbe, et al. Monocyte deactivation in septic patients: restoration by IFN-gamma treatment. Nat Med. 1997;3:678–81.
18. Volk, H., D., P. Reinke, and W. D. Docke. Clinical aspects: from systemic inflammation to 'immunoparalysis'. Chem. Immunol. 2000;74:162–77
19. Greenspan, L., B. A. McLellan, and H. Greig. Abbreviated injury scale and injury severity score: a scoring chart. J. Trauma. 1985;25:60–4.
20. American College of Chest Physicians—Society of Critical Care Medicine Consensus Conference. Definitions for sepsis and organ failure and guidelines for the use of innovative therapies in sepsis. Crit. Care Med. 1992;20:864–875.
21. Mosmann, T. Rapid colometric assay for cellular growth and survival: Application to proliferation and cytotoxity assays. J. Immunol. Methods. 1983;65:55–63.
22. Randow, F., U. Syrbe, C. Meisel, et al. Mechanism of endotoxin desensitization: Involvement of interleukin 10 and transforming growth factor β. J. Exp. Med. 1985;181:1887–92
23. Zweigner, J., H. J. Gramm, O. C. Singer, K. Wegscheider, and R. R. Schumann. High concentrations of lipopolysaccharide-binding protein in serum of patients with severe sepsis or septic shock inhibit the lipopolysaccharide response in human monocytes. Blood. 2001;98:3800–8
24. Ertel, W., M. Keel, R. Neidhardt, J. P. Kremer, U. Ungethuem, and O. Trentz. Inhibition of the defense system stimulating interleukin-12 interferon-γ pathway during critical illness. Blood 1997;89:1612–20
25. Majetschak, M., J. Borgermann, C. Waydhas, U. Obertacke, D. Nast-Kolb, and F. U. Schade. Diminished endotoxin induced whole blood TNF-α production and its relation to systemic concentrations of interleukin-4, interleukin-10 and transforming growth factor-β1 in multiply injured patients. Crit. Care Med. 2000; 28:1847–54
26. Takada, K., H. Nasu, N. Hibi, et al. Serum concentrations of free ubiquitin and multiubiquitin chains. Clin. Chem. 1997;43:1188–95
27. Majetschak, M., Laub, M., Meyer, H. E., and H. P. Jennissen. The ubiquityl-Calmodulin-Synthetase system from Rabbit Reticulocytes: Isolation of the Ubiquitin Binding First Component, a Truncated Form of the Ubiquitin Activating Enzyme. Eur. J. Biochem. 1998; 255: 482–491
28. Brandtzaeg, P., Osnes, L., Ovstebo, R., Joo, G. B., Westvik, A. B., and P. Kierulf. Net inflammatory capacity of human septic shock plasma evaluated by a monocyte-based target cell assay: identification of interleukin-10 as a major functional deactivator of human monocytes. J Exp Med 1996; 184:51–60
29. Majetschak M., R. Flach, E. Kreuzfelder, et al. The extent of traumatic damage determines a graded depression of the endotoxin responsiveness of peripheral blood mononuclear cells from patients with blunt injuries. Crit. Care Med. 1999;27: 313–318
30. Majetschak M, Krehmeier U, Bardenheuer M, Denz C, Quintel M, Voggenreiter G, Obertacke U. Extracellular ubiquitin inhibits the TNFα response to endotoxin in peripheral blood mononuclear cells and regulates endotoxin hyporesponsiveness in critical illness. Blood Oct. 24, 2002; [epub ahead of print], Blood, March 2003.

What is claimed is:

1. A method of treating or reducing fluid exiravasation after trauma and/or hemorrhage in a mammal comprising administering to said mammal an effective amount of ubiquitin.

2. The method of claim 1 wherein the trauma and/or hemorrhage is the result of blunt trauma injury.

3. The method of claim 1 wherein the trauma and/or hemorrhage results in shock.

4. The method of claim 1 wherein the trauma and/or hemorrhage results in tissue edema and erythema formation.

5. The method of claim 1 wherein the mammal is a human.

6. The method of claim 1 wherein the effective amount is between 0.01 and 10 mg/kg body weight.

7. The method of claim 2 wherein the effective amount is between 0.01 and 10 mg/kg body weight.

8. The method of claim 3 wherein the effective amount is between 0.01 and 10 mg/kg body weight.

9. The method of claim 4 wherein the effective amount is between 0.01 and 10 mg/kg body weight.

10. The method of claim 5 wherein the effective amount is between 0.01 and 10 mg/kg body weight.

11. The method of claim 1 wherein the ubiquitin is administered intravenously.

12. The method of claim 2 wherein the ubiquitin is administered intravenously.

13. The method of claim 3 wherein the ubiquitin is administered intravenously.

14. The method of claim 4 wherein the ubiquitin is administered intravenously.

15. The method of claim 5 wherein the ubiquitin is administered intravenously.

16. The method of claim 6 wherein the ubiquitin is administered intravenously.

17. The method of claim 7 wherein the ubiquitin is administered intravenously.

18. The method of claim 8 wherein the ubiquitin is administered intravenously.

19. The method of claim 9 wherein the ubiquitin is administered intravenously.

20. The method of claim 10 wherein the ubiquitin is administered intravenously.

\* \* \* \* \*